US007101940B2

(12) United States Patent
Schottek et al.

(10) Patent No.: US 7,101,940 B2
(45) Date of Patent: Sep. 5, 2006

(54) CHEMICAL COMPOUND, METHOD FOR THE PRODUCTION THEREOF AND ITS USE IN CATALYST SYSTEMS FOR PRODUCING POLYOLEFINS

(75) Inventors: Jörg Schottek, Frankfurt (DE); Heike Gregorius, Koblenz (DE); David Fischer, Breunigweiler (DE); Iris Kuellmer, Frankfurt (DE)

(73) Assignee: Basell Polyolefine GmbH, Frankfurt (DE)

( * ) Notice: Subject to any disclaimer, the term of this patent is extended or adjusted under 35 U.S.C. 154(b) by 0 days.

(21) Appl. No.: 10/168,719

(22) PCT Filed: Dec. 21, 2000

(86) PCT No.: PCT/EP00/13096

§ 371 (c)(1),
(2), (4) Date: Jun. 24, 2002

(87) PCT Pub. No.: WO01/48035

PCT Pub. Date: Jul. 5, 2001

(65) Prior Publication Data

US 2003/0013913 A1   Jan. 16, 2003

(30) Foreign Application Priority Data

Dec. 23, 1999 (DE) ................. 199 62 910

(51) Int. Cl.
| *C08F 4/52* | (2006.01) |
| *C08F 4/76* | (2006.01) |
| *B01J 31/14* | (2006.01) |
| *C07C 211/63* | (2006.01) |
| *C07F 5/02* | (2006.01) |

(52) U.S. Cl. ............... 526/134; 526/141; 526/153; 526/160; 526/943; 502/202; 502/200; 502/114; 502/103; 564/8; 564/282; 564/281

(58) Field of Classification Search ............ 568/1, 568/6; 502/123, 118, 202, 200, 114, 103; 526/131, 133, 134, 135, 141, 160, 153; 556/7; 564/8, 282, 281
See application file for complete search history.

(56) References Cited

U.S. PATENT DOCUMENTS

| 5,414,064 | A |   | 5/1995 | Lux et al. ............... 526/215 |
| 5,565,534 | A |   | 10/1996 | Aulbach et al. ........... 526/160 |
| 5,608,009 | A | * | 3/1997 | Machida et al. ........... 525/247 |
| 5,770,753 | A |   | 6/1998 | Küber et al. .............. 556/11 |
| 6,127,563 | A | * | 10/2000 | Chen et al. ............... 556/21 |
| 6,169,208 | B1 | * | 1/2001 | Lee ........................ 568/6 |
| 6,177,526 | B1 | * | 1/2001 | Fritze ..................... 526/128 |
| 6,271,165 | B1 | * | 8/2001 | Jacobsen et al. .......... 502/104 |
| 6,444,606 | B1 |   | 9/2002 | Bingel et al. ............. 502/152 |

FOREIGN PATENT DOCUMENTS

| DE | 197 44 102 |   | 4/1999 |
| DE | 197 57 540 |   | 6/1999 |
| DE | 197 57 540 A1 | * | 6/1999 |
| DE | 198 04 970 |   | 8/1999 |
| EP | 0 129 368 |   | 12/1984 |
| EP | 0 416 815 |   | 3/1991 |
| EP | 0 545 304 |   | 6/1993 |
| EP | 0 561 479 |   | 9/1993 |
| EP | 0 576 970 |   | 1/1994 |
| EP | 0 632 063 |   | 1/1995 |
| EP | 0 659 758 |   | 6/1995 |
| EP | 0 661 300 |   | 7/1995 |
| EP | 0 710 663 |   | 5/1996 |
| EP | 0 768 320 |   | 4/1997 |
| JP | 5295030 |   | 4/1992 |
| JP | 9-295984 A | * | 11/1997 |
| JP | 9-295985 A | * | 11/1997 |
| JP | 11286491 |   | 10/1999 |
| WO | WO 91/09882 |   | 7/1991 |
| WO | WO 93/11172 |   | 6/1993 |

(Continued)

OTHER PUBLICATIONS

Maehama et al. "Interation between cationic zirconium alkyl complexes ad fluorine-substituted BPh4 anions in ion-pair metallocene catalyst systems" Kobunshi Ronbunshu vol. 51 No. 10 (1994) pp. 670-675.

(Continued)

*Primary Examiner*—David W. Wu
*Assistant Examiner*—Rip A. Lee
(74) *Attorney, Agent, or Firm*—Novak Druce & Quigg LLP

(57) ABSTRACT

The invention relates to a chemical compound of formula (I), wherein $M^1$ represents an element selected from main groups II, III or IV of the periodic table of elements; x is equal to 1, 2, 3 or 4; y is equal to 2, 3 or 4, and; A represents a cation of main group V of the periodic table of elements; $R^1$ is the same or different and represents a branched or unbranched linear or cyclic $C_1$–$C_{40}$ group that contains carbon; $R^2$ is the same or different and represents a branched or unbranched linear or cyclic $C_1$–$C_{40}$ group that contains carbon; $R^3$ represents a branched or unbranched linear or cyclic $C_1$–$C_{40}$ group that contains carbon, and; $R^4$ represents a hydrogen atom; whereby $R^2$ and $R^3$ are always different from one another (I)

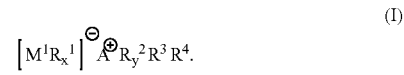

14 Claims, No Drawings

| | FOREIGN PATENT DOCUMENTS | |
|---|---|---|
| WO | WO 96/23005 | 8/1996 |
| WO | WO 96/27439 | 9/1996 |
| WO | WO 97/35893 | 10/1997 |
| WO | WO 97/35893 A1 * | 10/1997 |
| WO | WO 98/22486 | 5/1998 |
| WO | WO 98/40419 | 9/1998 |
| WO | WO 99/41289 | 8/1999 |
| WO | WO 99/42467 A1 * | 8/1999 |
| WO | WO 99/45047 | 9/1999 |

OTHER PUBLICATIONS

Vandeberg et al. "Studies in the Tetraarylborates" Analytica Chimca Acta vol. 44 (1969) pp. 175-183.

Bochmann et al. "Cationic titanium alkyls as alkane polymerization catalysts: solvent and anion dependence" Journal of Organometallic Chemistry vol. 424 (1992) pp. C5-C7.

* cited by examiner

CHEMICAL COMPOUND, METHOD FOR THE PRODUCTION THEREOF AND ITS USE IN CATALYST SYSTEMS FOR PRODUCING POLYOLEFINS

The present invention relates to chemical compounds which have an ionic structure and in combination with an organometallic transition metal compound form a catalyst system which is advantageously used for the polymerization of olefins.

Ziegler-type catalysts based on angled metallocenes of metals of transition group IV form a new generation of industrially useful catalysts for the polymerization of α-olefins (H. H. Brintzinger, D. Fischer, R. Mülhaupt, R. Rieger, R. Waymouth, Angew. Chem. 1995, 107, 1255–1283).

In order to obtain an active catalyst system, the metallocene complex is treated with a large excess of methylaluminoxane (MAO) (H. Sinn, W. Kaminsky, Adv. Organomet. Chem., 1980, 18, 99). Apart from the high cocatalyst costs, this has the disadvantage of a high aluminum content in the polymer obtained. For this reason, new activation methods which make do without a superstoichiometric amount of activator have been developed.

The synthesis of "cation-like" metallocene polymerization catalysts is described in J. Am. Chem. Soc. 1991, 113, 3623. Here, the alkyl group is abstracted from an alkylmetallocene compound by means of trispentafluorophenylborane which is used in a stoichiometric amount relative to the metallocene.

EP-A-0,427,697 claims this synthetic principle and a corresponding catalyst system comprising an uncharged metallocene species (e.g. $Cp_2ZrMe_2$), a Lewis acid (e.g. $B(C_6F_5)_3$) and aluminum alkyls. A method of preparing salts of the formula $LMX^+ XA^-$ according to the above-described principle is claimed in EP-A-0,520,732.

EP-A-0,558,158 describes zwitterionic catalyst systems which are prepared from dialkyl-metallocene compounds and salts of the formula $[R_3NH]^+[BPh_4]^-$. The reaction of such a salt with, for example, $Cp_2^*ZrMe_2$ results in protolysis with elimination of methane to give a methyl-zirconocene cation as an intermediate. This reacts by C—H activation to give the zwitterion $Cp_2^*Zr^+\text{-}(m\text{-}C_6H_4)\text{-}BPh_3^-$. Here, the Zr atom is covalently bound to a carbon atom of the phenyl ring and is stabilized by an agostic hydrogen bond.

U.S. Pat. No. 5,348,299 claims corresponding systems and uses dimethylanilinium salts with perfluorinated tetraphenylborates.

Apart from the activating action of the borate salts, their ligand sphere also exercises an important effect on the reaction equilibrium. Ligands which are too bulky substantially prevent dimerization of the metallocenium fragments and thus displace the equilibrium in the direction of the catalytically active species. The mononuclear borate anions described hitherto have four aryl ligands and can have an influence on the reaction equilibrium by means of the incorporation of bulky groups on the ligand (WO 95/24268). Disadvantages of these systems are the complicated syntheses and the extreme sensitivity of the resulting metallocenium complexes.

In addition, most of the starting materials are suspected of being carcinogenic, teratogenic or extremely toxic. This cannot be ruled out for the resulting products. Furthermore, the sometimes extreme insolubility of the ammonium tetraphenylborates described hitherto leads to very incompletely reacted catalyst systems. This has direct effects on the productivities of the catalyst systems based on the amount of metallocene and cocatalyst used. This important criterion leads to high costs and thus to only limited commercial utilization.

WO 97/35893 describes highly soluble activators for olefin polymerization catalysts which are particularly suitable for solution polymerization processes. However, systems which are particularly well suited to solution polymerization processes are generally not suitable for supported catalysts because of the good solubility of the components.

It is an object of the present invention to provide chemical compounds which are suitable as activators for catalyst systems for preparing polyolefins but do not suffer from the abovementioned disadvantages and, in particular, are not problematical in terms of health and have a solubility which is sufficient for application to a support but is not so high that the supported catalyst loses active component in the polymerization process.

We have found that this object is achieved by a chemical compound of the formula I,

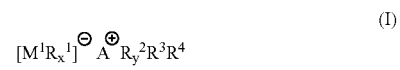

where
$M^1$ is an element of main group II, III or IV of the Periodic Table of the Elements,
x is 1, 2, 3 or 4,
y is 2, 3 or 4, and
A is a cation of main group V of the Periodic Table of the Elements,
$R^1$ are identical or different and are each a branched or unbranched, linear or cyclic $C_1$–$C_{40}$ group,
$R^2$ are identical or different and are each a branched or unbranched, linear or cyclic $C_1$–$C_{40}$ group,
$R^3$ is a branched or unbranched, linear or cyclic $C_1$–$C_{40}$ group and
$R^4$ is a hydrogen atom, where $R^2$ and $R^3$ are always different from one another and the compounds
decyldi(methyl)ammonium tetrakis(pentafluorophenyl)borate,
dodecyldi(methyl)ammonium tetrakis(pentafluorophenyl)borate,
tetradecyldi(methyl)ammonium tetrakis(pentafluorophenyl)borate,
hexadecyldi(methyl)ammonium tetrakis(pentafluorophenyl)borate,
octadecyldi(methyl)ammonium tetrakis(pentafluorophenyl)borate,
eicosyldi(methyl)ammonium tetrakis(pentafluorophenyl)borate,
methyldi(decyl)ammonium tetrakis(pentafluorophenyl)borate,
methyldi(dodecyl)ammonium tetrakis(pentafluorophenyl)borate,
methyldi(tetradecyl)ammonium tetrakis(pentafluorophenyl)borate,
methyldi(hexadecyl)ammonium tetrakis(pentafluorophenyl)borate,
methyldi(octadecyl)ammonium tetrakis(pentafluorophenyl)borate,
methyldi(eicosyl)ammonium tetrakis(pentafluorophenyl)borate, decyldi(n-butyl)ammonium tetrakis(pentafluorophenyl)borate,
dodecyldi(decyl)ammonium tetrakis(pentafluorophenyl)borate,
octadecyldi(decyl)ammonium tetrakis(pentafluorophenyl)borate,
N,N-didodecylanilinium tetrakis(pentafluorophenyl)borate,
N-methyl-N-dodecylanilinium tetrakis(pentafluorophenyl)borate,
N,N-di(octadecyl)(2,4,6-trimethylanilinium tetrakis(pentafluorophenyl)borate,
cyclohexyldi(dodecyl)ammonium tetrakis(pentafluorophenyl)borate,
N,N-dimethylanilinium tetra(phenyl)borate,
N,N-diethylanilinium tetra(phenyl)borate,
N,N-2,4,6-pentamethylanilinium tetra(phenyl)borate and
dimethylanilinium tetrakis(pentafluorophenyl)borate are excepted.

Preferably, at least one radical $R^2$, $R^3$ is a branched or cyclic group having from 3 to 40 carbon atoms, in particular from 6 to 30 carbon atoms.

Preference is given to compounds which conform to the formula (II),

(II)

in which
$M^1$ is boron or aluminum,
x is 4,
y is 2 and
A is a cation of main group V of the Periodic Table of the Elements,
$R^1$ are each $C_6$–$C_{40}$-haloaryl, $C_6$–$C_{40}$-aryloxy, $C_7$–$C_{40}$-arylalkyl, $C_7$–$C_{40}$-haloarylalkyl, $C_7$–$C_{40}$-haloalkylaryl or $C_4$–$C_{40}$-cycloalkyl,
$R^2$ are each $C_1$–$C_{20}$-alkyl, $C_1$–$C_{20}$-haloalkyl, $C_1$–$C_{10}$-alkoxy, $C_6$–$C_{40}$-haloaryl, $C_7$–$C_{40}$-alkylaryl, $C_7$–$C_{40}$-arylalkyl, $C_7$–$C_{40}$-haloarylalkyl, $C_7$–$C_{40}$-haloalkylaryl or substituted or unsubstituted $C_4$–$C_{40}$-cycloalkyl,
$R^3$ is $C_1$–$C_{20}$-alkyl, $C_1$–$C_{20}$-haloalkyl, $C_1$–$C_{10}$-alkoxy, $C_6$–$C_{40}$-haloaryl, $C_7$–$C_{40}$-alkylaryl, $C_7$–$C_{40}$-arylalkyl, $C_7$–$C_{40}$-haloarylalkyl, $C_7$–$C_{40}$-haloalkylaryl or substituted or unsubstituted $C_4$–$C_{40}$-cycloalkyl,
$R^4$ is a hydrogen atom, where $R^2$ and $R^3$ always have to be different from one another.

Particular preference is given to compounds in which $M^1$=boron and which have the formula (IIa),

(IIa)

in which
x is 4,
y is 2 and
A is nitrogen and
$R^1$ are each $C_6$–$C_{40}$-haloaryl, $C_6$–$C_4$O-aryloxy, $C_7$–$C_{40}$-arylalkyl, $C_7$–$C_{40}$-haloarylalkyl, $C_7$–$C_{40}$-haloalkylaryl or $C_4$–$C_{40}$-cycloalkyl,
$R^2$ are each $C_1$–$C_6$-alkyl and
$R^3$ is $C_3$–$C_9$-cycloalkyl which may be substituted by $C_1$–$C_{20}$-alkyl, in particular $C_1$–$C_5$-alkyl, $C_1$–$C_{20}$-haloalkyl, $C_1$–$C_{10}$-alkoxy, $C_6$–$C_{40}$-haloaryl, $C_7$–$C_{40}$-alkylaryl, $C_7$–$C_{40}$-arylalkyl, $C_7$–$C_{40}$-haloarylalkyl or $C_7$–$C_{40}$-haloalkylaryl, or is $C_7$–$C_{20}$-alkylaryl or $C_7$–$C_{20}$-arylalkyl and $R^4$ is a hydrogen atom, where $R^2$ and $R^3$ always have to be different from one another.

Particularly preferred but nonlimiting examples-of novel chemical compounds of the formulae (I) and (II) are:
N,N-dimethylcyclohexylammonium tetrakis(pentafluorophenyl)borate,
N,N-dimethylcyclohexylammonium tetrakis(2,3,4,6-tetrafluorophenyl)borate,
N,N-dimethylcyclohexylammonium tetrakis(2,3,5,6-tetrafluorophenyl)borate,
N,N-dimethylcyclohexylammonium tetrakis(2,3,5-trifluorophenyl)borate,
N,N-dimethylcyclohexylammonium tetrakis(2,3,6-trifluorophenyl)borate,
N,N-dimethylcyclohexylammonium tetrakis(1,3-difluorophenyl)borate,
N,N-dimethylcyclohexylammonium tetrakis(2,3,5,6-tetrafluoro-4-methylphenyl)borate,
N,N-dimethylcyclohexylammonium tetrakis(2,3,4,6-tetrafluoro-5-methylphenyl)borate,
N,N-dimethylcyclohexylammonium tetrakis(2,3,5-trifluorophenyl)borate,
N,N-dimethylcyclohexylammonium tetrakis(2,4,5-trifluoro-6-methylphenyl)borate,
N,N-dimethylcyclohexylammonium tetrakis(2,3,6-trifluoro-4-methylphenyl)borate,
N,N-dimethylcyclohexylammonium tetrakis(2,4,6-trifluoro-3-methylphenyl)borate,
N,N-dimethylcyclohexylammonium tetrakis(2,6-difluoro-3-methylphenyl)borate,
N,N-dimethylcyclohexylammonium tetrakis(2,4-difluoro-5-methylphenyl)borate,
N,N-dimethylcyclohexylammonium tetrakis(3,5-difluoro-2-methylphenyl)borate,
N,N-dimethylcyclohexylammonium tetrakis(4-methoxy-2,3,5,6-tetrafluorophenyl)borate,
N,N-dimethylcyclohexylammonium tetrakis(3-methoxy-2,4,5,6-tetrafluorophenyl)borate,
N,N-dimethylcyclohexylammonium tetrakis(2-methoxy-3,4,5,6-tetrafluorophenyl)borate,
N,N-diethylcyclohexylammonium tetrakis(pentafluorophenyl)borate,
N,N-diethylcyclohexylammonium tetrakis(2,3,4,6-tetrafluorophenyl)borate,
N,N-diethylcyclohexylammonium tetrakis(2,3,5,6-tetrafluorophenyl)borate,
N,N-diethylcyclohexylammonium tetrakis(2,3,5-trifluorophenyl)borate,
N,N-diethylcyclohexylammonium tetrakis(2,3,6-trifluorophenyl)borate,
N,N-diethylcyclohexylammonium tetrakis(1,3-difluorophenyl)borate,
N,N-diethylcyclohexylammonium tetrakis(2,3,5,6-tetrafluoro-4-methylphenyl)borate,
N,N-diethylcyclohexylammonium tetrakis(2,3,4,6-tetrafluoro-5-methylphenyl)borate,
N,N-diethylcyclohexylammonium tetrakis(2,3,5-trifluorophenyl)borate,
N,N-diethylcyclohexylammonium tetrakis(2,4,5-trifluoro-6-methylphenyl)borate, N,N-diethylcyclohexylammonium tetrakis(2,3,6-trifluoro-4-methylphenyl)borate,
N,N-diethylcyclohexylammonium tetrakis(2,4,6-trifluoro-3-methylphenyl)borate,
N,N-diethylcyclohexylammonium tetrakis(2,6-difluoro-3-methylphenyl)borate,
N,N-diethylcyclohexylammonium tetrakis(2,4-difluoro-5-methylphenyl)borate,
N,N-diethylcyclohexylammonium tetrakis(3,5-difluoro-2-methylphenyl)borate,
N,N-diethylcyclohexylammonium tetrakis(4-methoxy-2,3,5,6-tetrafluorophenyl)borate,
N,N-diethylcyclohexylammonium tetrakis(3-methoxy-2,4,5,6-tetrafluorophenyl)borate,
N,N-diethylcyclohexylammonium tetrakis(2-methoxy-3,4,5,6-tetrafluorophenyl)borate,
N,N-diisopropylcyclohexylammonium tetrakis(pentafluorophenyl)borate,
N,N-diisopropylcyclohexylammonium tetrakis(2,3,4,6-tetrafluorophenyl)borate,
N,N-diisopropylcyclohexylammonium tetrakis(2,3,5,6-tetrafluorophenyl)borate,
N,N-diisopropylcyclohexylammonium tetrakis(2,3,5-trifluorophenyl)borate,
N,N-diisopropylcyclohexylammonium tetrakis(2,3,6-trifluorophenyl)borate,
N,N-diisopropylcyclohexylammonium tetrakis(1,3-difluorophenyl)borate,
N,N-diisopropylcyclohexylammonium tetrakis(2,3,5,6-tetrafluoro-4-methylphenyl)borate,
N,N-diisopropylcyclohexylammonium tetrakis(2,3,4,6-tetrafluoro-5-methylphenyl)borate,
N,N-diisopropylcyclohexylammonium tetrakis(2,3,5-trifluorophenyl)borate,
N,N-diisopropylcyclohexylammonium tetrakis(2,4,5-trifluoro-6-methylphenyl)borate,
N,N-diisopropylcyclohexylammonium tetrakis(2,3,6-trifluoro-4-methylphenyl)borate,
N,N-diisopropylcyclohexylammonium tetrakis(2,4,6-trifluoro-3-methylphenyl)borate,
N,N-diisopropylcyclohexylammonium tetrakis(2,6-difluoro-3-methylphenyl)borate,
N,N-diisopropylcyclohexylammonium tetrakis(2,4-difluoro-5-methylphenyl)borate,
N,N-diisopropylcyclohexylammonium tetrakis(3,5-difluoro-2-methylphenyl)borate,
N,N-diisopropylcyclohexylammonium tetrakis(4-methoxy-2,3,5,6-tetrafluorophenyl)borate,
N,N-diisopropylcyclohexylammonium tetrakis(3-methoxy-2,4,5,6-tetrafluorophenyl)borate,
N,N-diisopropylcyclohexylammonium tetrakis(2-methoxy-3,4,5,6-tetrafluorophenyl)borate;
N,N-diethylbenzylammonium tetrakis(pentafluorophenyl)borate,
N,N-diisopropylbenzylammonium tetrakis(pentafluorophenyl)borate,
N,N-diethylbenzylammonium tetrakis(2,3,4,6-tetrafluorophenyl)borate,
N,N-diethylbenzylammonium tetrakis(2,3,5,6-tetrafluorophenyl)borate,
N,N-diethylbenzylammonium tetrakis(2,3,5-trifluorophenyl)borate,
N,N-diethylbenzylammonium tetrakis(2,3,6-trifluorophenyl)borate,
N,N-diethylbenzylammonium tetrakis(1,3-difluorophenyl)borate,
N,N-diethylbenzylammonium tetrakis(2,3,5,6-tetrafluoro-4-methylphenyl)borate,
N,N-diethylbenzylammonium tetrakis(2,3,4,6-tetrafluoro-5-methylphenyl)borate,
N,N-diethylbenzylammonium tetrakis(2,3,5-trifluorophenyl)borate,
N,N-diethylbenzylammonium tetrakis(2,4,5-trifluoro-6-methylphenyl)borate,
N,N-diethylbenzylammonium tetrakis(2,3,6-trifluoro-4-methylphenyl)borate,
N,N-diethylbenzylammonium tetrakis(2,4,6-trifluoro-3-methylphenyl)borate,
N,N-diethylbenzylammonium tetrakis(2,6-difluoro-3-methylphenyl)borate,
N,N-diethylbenzylammonium tetrakis(2,4-difluoro-5-methylphenyl)borate,
N,N-diethylbenzylammonium tetrakis(3,5-difluoro-2-methylphenyl)borate,
N,N-diethylbenzylammonium tetrakis(4-methoxy-2,3,5,6-tetrafluorophenyl)borate,
N,N-diethylbenzylammonium tetrakis(3-methoxy-2,4,5,6-tetrafluorophenyl)borate,
N,N-diethylbenzylammonium tetrakis(2-methoxy-3,4,5,6-tetrafluorophenyl)borate
N,N-dimethylbenzylammonium tetrakis(pentafluorophenyl)borate,
N,N-dimethylbenzylammonium tetrakis(2,3,4,6-tetrafluorophenyl)borate,
N,N-dimethylbenzylammonium tetrakis(2,3,5,6-tetrafluorophenyl)borate,
N,N-dimethylbenzylammonium tetrakis(2,3,5-trifluorophenyl)borate,
N,N-dimethylbenzylammonium tetrakis(2,3,6-trifluorophenyl)borate,
N,N-dimethylbenzylammonium tetrakis(1,3-difluorophenyl)borate,
N,N-dimethylbenzylammonium tetrakis(2,3,5,6-tetrafluoro-4-methylphenyl)borate,
N,N-dimethylbenzylammonium tetrakis(2,3,4,6-tetrafluoro-5-methylphenyl)borate,
N,N-dimethylbenzylammonium tetrakis(2,3,5-trifluorophenyl)borate,
N,N-dimethylbenzylammonium tetrakis(2,4,5-trifluoro-6-methylphenyl)borate,
N,N-dimethylbenzylammonium tetrakis(2,3,6-trifluoro-4-methylphenyl)borate,
N,N-dimethylbenzylammonium tetrakis(2,4,6-trifluoro-3-methylphenyl)borate,
N,N-dimethylbenzylammonium tetrakis(2,6-difluoro-3-methylphenyl)borate,
N,N-dimethylbenzylammonium tetrakis(2,4-difluoro-5-methylphenyl)borate,
N,N-dimethylbenzylammonium tetrakis(3,5-difluoro-2-methylphenyl)borate,
N,N-dimethylbenzylammonium tetrakis(4-methoxy-2,3,5,6-tetrafluorophenyl)borate,
N,N-dimethylbenzylammonium tetrakis(3-methoxy-2,4,5,6-tetrafluorophenyl)borate,
N,N-dimethylbenzylammonium tetrakis(2-methoxy-3,4,5,6-tetrafluorophenyl)borate
N,N-dimethylcyclohexylmethylammonium tetrakis(pentafluorophenyl)borate
N,N-diethylcyclohexylmethylammonium tetrakis(pentafluorophenyl)borate
N,N-diethylcyclohexylethylammonium tetrakis(pentafluorophenyl)borate N,N-dimethylcyclohexylethylammonium tetrakis(pentafluorophenyl)borate
N,N-diisopropylcyclohexylmethylammonium tetrakis(pentafluorophenyl)borate
N,N-diisopropylcyclohexylethylammonium tetrakis(pentafluorophenyl)borate
N,N-dimethylcyclohexylpropylammonium tetrakis(pentafluorophenyl)borate
N,N-diethylcyclohexylpropylammonium tetrakis(pentafluorophenyl)borate
N,N-dimethylcyclohexylpropylammonium tetrakis(pentafluorophenyl)borate
N,N-diisopropylcyclohexylpropylammonium tetrakis(pentafluorophenyl)borate
N,N-diisobutylcyclohexylpropylammonium tetrakis(pentafluorophenyl)borate
N,N-diethylcyclohexylbutylammonium tetrakis(pentafluorophenyl)borate
N,N-dimethylcyclohexylbutylammonium tetrakis(pentafluorophenyl)borate
N,N-diisopropylcyclohexylbutylammonium tetrakis(pentafluorophenyl)borate
N,N-diisobutylcyclohexylbutylammonium tetrakis(pentafluorophenyl)borate
N,N-diethylcyclohexylhexylammonium tetrakis(pentafluorophenyl)borate
N,N-dimethylcyclohexylhexylammonium tetrakis(pentafluorophenyl)borate
N,N-diisopropylcyclohexylhexylammonium tetrakis(pentafluorophenyl)borate
N,N-diisobutylcyclohexylhexylammonium tetrakis(pentafluorophenyl)borate
N,N-dibutylcyclohexylmethylammonium tetrakis(pentafluorophenyl)borate
N,N-dibutylcyclohexylethylammonium tetrakis(pentafluorophenyl)borate
N,N-dibutylcyclohexylpropylammonium tetrakis(pentafluorophenyl)borate
N,N-dibutylcyclohexylbutylammonium tetrakis(pentafluorophenyl)borate
N,N-dibutylcyclohexylhexylammonium tetrakis(pentafluorophenyl)borate
N,N-dimethyl-4-methylbenzylammonium tetrakis(pentafluorophenyl)borate
N,N-diethyl-4-methylbenzylammonium tetrakis(pentafluorophenyl)borate
N,N-diisopropyl-4-methylbenzylmethylammonium tetrakis(pentafluorophenyl)borate
N,N-diisobutyl-4-methylbenzylpropylammonium tetrakis(pentafluorophenyl)borate
N,N-diethyl-3-methylbenzylammonium tetrakis(pentafluorophenyl)borate
N,N-diisopropyl-3-methylbenzylammonium tetrakis(pentafluorophenyl)borate
N,N-diisobutyl-3-methylbenzylammonium tetrakis(pentafluorophenyl)borate
N,N-diethyl-2-methylbenzylammonium tetrakis(pentafluorophenyl)borate
N,N-diisopropyl-2-methylbenzylammonium tetrakis(pentafluorophenyl)borate
N,N-diisobutyl-2-methylbenzylammonium tetrakis(pentafluorophenyl)borate
N,N-diethyl-3,5-dimethylbenzylammonium tetrakis(pentafluorophenyl)borate
N,N-diisopropyl-3,5-dimethylbenzylammonium tetrakis(pentafluorophenyl)borate
N,N-diisobutyl-3,5-dimethylbenzylammonium tetrakis(pentafluorophenyl)borate
N,N-diethyl-2,4-dimethylbenzylammonium tetrakis(pentafluorophenyl)borate
N,N-diisopropyl-2,4-dimethylbenzylammonium tetrakis(pentafluorophenyl)borate
N,N-diisobutyl-2,4-dimethylbenzylammonium tetrakis(pentafluorophenyl)borate
N,N-dimethyl-4-ethylbenzylammonium tetrakis(pentafluorophenyl)borate
N,N-diethyl-4-ethylbenzylammonium tetrakis(pentafluorophenyl)borate
N,N-diisopropyl-4-ethylbenzylmethylammonium tetrakis(pentafluorophenyl)borate
N,N-diisobutyl-4-ethylbenzylpropylammonium tetrakis(pentafluorophenyl)borate
N,N-diethyl-3-ethylbenzylammonium tetrakis(pentafluorophenyl)borate
N,N-diisopropyl-3-propylbenzylammonium tetrakis(pentafluorophenyl)borate
N,N-diisobutyl-3-propylbenzylammonium tetrakis(pentafluorophenyl)borate
N,N-diethyl-2-propylbenzylammonium tetrakis(pentafluorophenyl)borate
N,N-diisopropyl-2-propylbenzylammonium tetrakis(pentafluorophenyl)borate
N,N-diisobutyl-2-propylbenzylammonium tetrakis(pentafluorophenyl)borate
N,N-diethyl-3,5-dipropylbenzylammonium tetrakis(pentafluorophenyl)borate
N,N-diisopropyl-3,5-dipropylbenzylammonium tetrakis(pentafluorophenyl)borate
N,N-diisobutyl-3,5-dipropylbenzylammonium tetrakis(pentafluorophenyl)borate
N,N-diethyl-2,4-dipropylbenzylammonium tetrakis(pentafluorophenyl)borate
N,N-diisopropyl-2,4-dipropylbenzylammonium tetrakis(pentafluorophenyl)borate
N,N-diisobutyl-2,4-dipropylbenzylammonium tetrakis(pentafluorophenyl)borate
N,N-diethyl-3-ethylbenzylammonium tetrakis(pentafluorophenyl)borate
N,N-diisopropyl-3-ethylbenzylammonium tetrakis(pentafluorophenyl)borate
N,N-diisobutyl-3-ethylbenzylammonium tetrakis(pentafluorophenyl)borate
N,N-diethyl-2-ethylbenzylammonium tetrakis(pentafluorophenyl)borate
N,N-diisopropyl-2-ethylbenzylammonium tetrakis(pentafluorophenyl)borate
N,N-diisobutyl-2-ethylbenzylammonium tetrakis(pentafluorophenyl)borate
N,N-diethyl-3,5-diethylbenzylammonium tetrakis(pentafluorophenyl)borate
N,N-diisopropyl-3,5-diethylbenzylammonium tetrakis(pentafluorophenyl)borate
N,N-diisobutyl-3,5-diethylbenzylammonium tetrakis(pentafluorophenyl)borate
N,N-diethyl-2,4-diethylbenzylammonium tetrakis(pentafluorophenyl)borate
N,N-diisopropyl-2,4-diethylbenzylammonium tetrakis(pentafluorophenyl)borate
N,N-diisobutyl-2,4-diethylbenzylammonium tetrakis(pentafluorophenyl)borate
N,N-diethyl-3-butylbenzylammonium tetrakis(pentafluorophenyl)borate N,N-diisopropyl-3-butylbenzylammonium tetrakis(pentafluorophenyl)borate
N,N-diisobutyl-3-butylbenzylammonium tetrakis(pentafluorophenyl)borate
N,N-diethyl-2-butylbenzylammonium tetrakis(pentafluorophenyl)borate
N,N-diisopropyl-2-butylbenzylammonium tetrakis(pentafluorophenyl)borate
N,N-diisobutyl-2-butylbenzylammonium tetrakis(pentafluorophenyl)borate
N,N-diethyl-3,5-dibutylbenzylammonium tetrakis(pentafluorophenyl)borate
N,N-diisopropyl-3,5-dibutylbenzylammonium tetrakis(pentafluorophenyl)borate
N,N-diisobutyl-3,5-dibutylbenzylammonium tetrakis(pentafluorophenyl)borate
N,N-diethyl-2,4-dibutylbenzylammonium tetrakis(pentafluorophenyl)borate
N,N-diisopropyl-2,4-dibutylbenzylammonium tetrakis(pentafluorophenyl)borate
N,N-diisobutyl-2,4-dibutylbenzylammonium tetrakis(pentafluorophenyl)borate
N,N-dimethylisopropylammonium tetrakis(pentafluorophenyl)borate,
N,N-dimethyl-2-butylammonium tetrakis(pentafluorophenyl)borate,
N,N-dimethyl-isobutylammonium tetrakis(pentafluorophenyl)borate,
N,N-dimethyl-2-methylbutylammonium tetrakis(pentafluorophenyl)borate,
N,N-dimethylcyclopentylammonium tetrakis(pentafluorophenyl)borate,
N,N-dimethyl-2-hexylammonium tetrakis(pentafluorophenyl)borate,
N,N-dimethyl-2-ethylbutylammonium tetrakis(pentafluorophenyl)borate,
N,N-dimethyl-2-methylhexylammonium tetrakis(pentafluorophenyl)borate,
N,N-dimethylmethylcyclohexylammonium tetrakis(pentafluorophenyl)borate,
N,N-dimethyl-2-ethylhexylammonium tetrakis(pentafluorophenyl)borate,
N,N-diethylisopropylammonium tetrakis(pentafluorophenyl)borate,
N,N-diethyl-2-butylammonium tetrakis(pentafluorophenyl)borate,
N,N-diethylisobutylammonium tetrakis(pentafluorophenyl)borate,
N,N-diethyl-2-methylbutylammonium tetrakis(pentafluorophenyl)borate,
N,N-diethyl-2-hexylammonium tetrakis(pentafluorophenyl)borate,
N,N-diethyl-2-ethylbutylammonium tetrakis(pentafluorophenyl)borate,
N,N-diethyl-2-methylhexylammonium tetrakis(pentafluorophenyl)borate,
N,N-diethylmethylcyclohexylammonium tetrakis(pentafluorophenyl)borate,
N,N-diethyl-2-ethylhexylammonium tetrakis(pentafluorophenyl)borate,
N-methyl-N-ethylisopropylammonium tetrakis(pentafluorophenyl)borate,
N-methyl-N-ethyl-2-butylammonium tetrakis(pentafluorophenyl)borate,
N-methyl-N-ethylisobutylammonium tetrakis(pentafluorophenyl)borate,
N-methyl-N-ethyl-2-methylbutylammonium tetrakis(pentafluorophenyl)borate,
N-methyl-N-ethylcyclopentylammonium tetrakis(pentafluorophenyl)borate,
N-methyl-N-ethyl-2-ethylbutylammonium tetrakis(pentafluorophenyl)borate,
N-methyl-N-ethylcyclohexylammonium tetrakis(pentafluorophenyl)borate,
N-methyl-N-ethyl-2-methylhexylammonium tetrakis(pentafluorophenyl)borate,
N-methyl-N-ethylmethylcyclohexylammonium tetrakis(pentafluorophenyl)borate,
N-methyl-N-ethylbenzylammonium tetrakis(pentafluorophenyl)borate,
N-methyl-N-ethyl-2-ethylhexylammonium tetrakis(pentafluorophenyl)borate,
N-methyldiisopropylammonium tetrakis(pentafluorophenyl)borate,
N-methylbis(2-butyl)ammonium tetrakis(pentafluorophenyl)borate,
N-methylbis(isobutyl)ammonium tetrakis(pentafluorophenyl)borate
N-methylbis(2-methylbutyl)ammonium tetrakis(pentafluorophenyl)borate,
N-methyldicyclopentylammonium tetrakis(pentafluorophenyl)borate,
N-methylbis(2-ethylbutyl)ammonium tetrakis(pentafluorophenyl)borate,
N-methyldicyclohexylammonium tetrakis(pentafluorophenyl)borate,
N-methylbis(2-methylhexyl)ammonium tetrakis(pentafluorophenyl)borate,
N-methylbis(methylcyclohexyl)ammonium tetrakis(pentafluorophenyl)borate,
N-methyldibenzylammonium tetrakis(pentafluorophenyl)borate,
N-methylbis(2-ethylhexyl)ammonium tetrakis(pentafluorophenyl)borate,
N-methylbis(dimethylcyclohexyl)ammonium tetrakis(pentafluorophenyl)borate,
N-ethyldiisopropylammonium tetrakis(pentafluorophenyl)borate,
N-ethylbis(2-butyl)ammonium tetrakis(pentafluorophenyl)borate,
N-ethylbis(isobutyl)ammonium tetrakis(pentafluorophenyl)borate,
N-ethylbis(2-methylbutyl)ammonium tetrakis(pentafluorophenyl)borate,
N-ethyldicyclopentylammonium tetrakis(pentafluorophenyl)borate,
N-ethylbis(2-ethylbutyl)ammonium tetrakis(pentafluorophenyl)borate,
N-ethyldicyclohexylammonium tetrakis(pentafluorophenyl)borate,
N-ethylbis(2-methylhexyl)ammonium tetrakis(pentafluorophenyl)borate,
N-ethylbis(methylcyclohexyl)ammonium tetrakis(pentafluorophenyl)borate,
N-ethyldi(benzyl)ammonium tetrakis(pentafluorophenyl)borate,
N-ethylbis(2-ethylhexyl)ammonium tetrakis(pentafluorophenyl)borate,
N-ethylbis(dimethylcyclohexyl)ammonium tetrakis(pentafluorophenyl)borate.

The preparation of a novel chemical compound of the formula (I) or (II) is carried out in the manner described in the literature. The reaction to form the ammonium hydrochloride salt is carried out by reacting the corresponding amine with hydrogen chloride. The further reaction to form the ammonium tetraphenylborate is carried out by reaction with the corresponding alkali metal borate or alkaline earth metal borate.

Nonlimiting examples of amines are:
N,N-dimethylcyclohexylamine, N,N-diethylcyclohexylamine,
N,N-dimethylisopropylamine, N,N-diethylbenzylamine,
N,N-dimethyl-p-toluidine, N,N-diethyl-p-toluidine
N,N-dimethylbenzylamine, N,N-diethylisopropylamine,
N,N-diisopropylmethylamine, N,N-diisopropylethylamine,
N,N-dimethylcyclopentylamine, N,N-dimethylcycloheptenylamine,
N,N-dimethylcyclooctanylamine, N,N-dimethylnonanoylamine,
N,N-diethylcyclopentylamine, N,N-diethylcycloheptenylamine,
N,N-diethylcyclooctanylamine, N,N-diethylnonanoylamine
N-benzyldimethylamine, N-benzyldiethylamine, N-benzylbutylamine,
N-benzyl-tert-butylamine, N'-benzyl-N,N-dimethylethylenediamine,
N-benzylethylenediamine, N-benzylisopropylamine,
N-benzylmethylamine, N-benzylethylamine,
N-benzyl-1-phenylethylamine, N-benzyl-2-phenylethylamine, or N-benzylpiperazine
N,N-dimethylisopropylamine, N,N-dimethyl-2-butylamine,
N,N-dimethylisobutylamine, N,N-dimethyl-2-pentylamine,
N,N-dimethyl-3-pentylamine, N,N-dimethyl-2-methylbutylamine,
N,N-dimethyl-3-methylbutylamine, N,N-dimethylcyclopentylamine,
N,N-dimethyl-2-hexylamine, N,N-dimethyl-3-hexylamine,
N,N-dimethyl-2-methylpentylamine,
N,N-dimethyl-3-methylpentylamine,
N,N-dimethyl-4-methylpentylamine, N,N-dimethyl-2-ethylbutylamine,
N,N-dimethylcyclohexylamine, N,N-dimethyl-2-heptylamine,
N,N-dimethyl-3-heptylamine, N,N-dimethyl-4-heptylamine,
N,N-dimethyl-2-methylhexylamine, N,N-dimethyl-3-methylhexylamine,
N,N-dimethyl-4-methylhexylamine, N,N-dimethyl-5-methylhexylamine,
N,N-dimethyl-2-ethylpentylamine, N,N-dimethyl-3-ethylpentylamine,
N,N-dimethyl-2-propylbutylamine, N,N-dimethylcycloheptylamine,
N,N-dimethylmethylcyclohexylamine, N,N-dimethylbenzylamine,
N,N-dimethyl-2-octylamine, N,N-dimethyl-3-octylamine
N,N-dimethyl-4-octylamine, N,N-dimethyl-2-methylheptylamine,
N,N-dimethyl-3-methylheptylamine,
N,N-dimethyl-4-methylheptylamine,
N,N-dimethyl-5-methylheptylamine,
N,N-dimethyl-6-methylheptylamine, N,N-dimethyl-2-ethylhexylamine,
N,N-dimethyl-3-ethylhexylamine, N,N-dimethyl-4-ethylhexylamine,
N,N-dimethyl-2-propylpentylamine, N,N-dimethylcyclooctylamine,
N,N-dimethyldimethylcyclohexylamine, N,N-diethylisopropylamine,
N,N-diethyl-2-butylamine, N,N-diethylisobutylamine,
N,N-diethyl-2-pentylamine, N,N-diethyl-3-pentylamine,
N,N-diethyl-2-methylbutylamine, N,N-diethyl-3-methylbutylamine,
N,N-diethylcyclopentylamine, N,N-diethyl-2-hexylamine,
N,N-diethyl-3-hexylamine, N,N-diethyl-2-methylpentylamine,
N,N-diethyl-3-methylpentylamine, N,N-diethyl-4-methylpentylamine,
N,N-diethyl-2-ethylbutylamine, N,N-diethylcyclohexylamine,
N,N-diethyl-2-heptylamine, N,N-diethyl-3-heptylamine,
N,N-diethyl-4-heptylamine, N,N-diethyl-2-methylhexylamine,
N,N-diethyl-3-methylhexylamine, N,N-diethyl-4-methylhexylamine,
N,N-diethyl-5-methylhexylamine, N,N-diethyl-2-ethylpentylamine,
N,N-diethyl-3-ethylpentylamine, N,N-diethyl-2-propylbutylamine,
N,N-diethylcycloheptylamine, N,N-diethylmethylcyclohexylamine,
N,N-diethylbenzylamine, N,N-diethyl-2-octylamine,
N,N-diethyl-3-octylamine, N,N-diethyl-4-octylamine,
N,N-diethyl-2-methylheptylamine, N,N-diethyl-3-methylheptylamine,
N,N-diethyl-4-methylheptylamine, N,N-diethyl-5-methylheptylamine,
N,N-diethyl-6-methylheptylamine, N,N-diethyl-2-ethylhexylamine,
N,N-diethyl-3-ethylhexylamine, N,N-diethyl-4-ethylhexylamine,
N,N-diethyl-2-propylpentylamine, N,N-diethylcyclooctylamine,
N,N-diethyldimethylcyclohexylamine,
N-methyl-N-ethylisopropylamine, N-methyl-N-ethyl-2-butylamine,
N-methyl-N-ethylisobutylamine, N-methyl-N-ethyl-2-pentylamine,
N-methyl-N-ethyl-3-pentylamine,
N-methyl-N-ethyl-2-methylbutylamine,
N-methyl-N-ethyl-3-methylbutylamine,
N-methyl-N-ethylcyclopentylamine, N-methyl-N-ethyl-2-hexylamine,
N-methyl-N-ethyl-3-hexylamine,
N-methyl-N-ethyl-2-methylpentylamine,
N-methyl-N-ethyl-3-methylpentylamine,
N-methyl-N-ethyl-4-methylpentylamine,
N-methyl-N-ethyl-2-ethylbutylamine,
N-methyl-N-ethyl-cyclohexylamine, N-methyl-N-ethyl-2-heptylamine,
N-methyl-N-ethyl-3-heptylamine
N-methyl-N-ethyl-4-heptylamine,
N-methyl-N-ethyl-2-methylhexylamine
N-methyl-N-ethyl-3-methylhexylamine,
N-methyl-N-ethyl-4-methylhexylamine,
N-methyl-N-ethyl-5-methylhexylamine,
N-methyl-N-ethyl-2-ethylpentylamine,
N-methyl-N-ethyl-3-ethylpentylamine,
N-methyl-N-ethyl-2-propylbutylamine,
N-methyl-N-ethylcycloheptylamine,
N-methyl-N-ethylmethylcyclohexylamine,
N-methyl-N-ethylbenzylamine, N-methyl-N-ethyl-2-octylamine,
N-methyl-N-ethyl-3-octylamine, N-methyl-N-ethyl-4-octylamine,
N-methyl-N-ethyl-2-methylheptylamine,
N-methyl-N-ethyl-3-methylheptylamine, N-methyl-N-ethyl-4-methylheptylamine,
N-methyl-N-ethyl-5-methylheptylamine,
N-methyl-N-ethyl-6-methylheptylamine,
N-methyl-N-ethyl-2-ethylhexylamine,
N-methyl-N-ethyl-3-ethylhexylamine,
N-methyl-N-ethyl-4-ethylhexylamine,
N-methyl-N-ethyl-2-propylpentylamine,
N-methyl-N-ethylcyclooctylamine,
N-methyl-N-ethyldimethylcyclohexylamine,
N-methyldiisopropylamine, N-methylbis(2-butyl)amine,
N-methylbis(isobutyl)amine, N-methylbis(2-pentyl)amine,
N-methylbis(3-pentyl)amine, N-methylbis(2-methylbutyl)amine,
N-methylbis(3-methylbutyl)amine, N-methyldicyclopentylamine,
N-methylbis(2-hexyl)amine, N-methylbis(3-hexyl)amine,
N-methylbis(2-methylpentyl)amine,
N-methylbis(3-methylpentyl)amine,
N-methylbis(4-methylpentyl)amine, N-methylbis(2-ethylbutyl)amine,
N-methyldicyclohexylamine, N-methylbis(2-heptyl)amine,
N-methylbis(3-heptyl)amine, N-methylbis(4-heptyl)amine,
N-methylbis(2-methylhexyl)amine, N-methylbis(3-methylhexyl)amine,
N-methylbis(4-methylhexyl)amine, N-methylbis(5-methylhexyl)amine,
N-methylbis(2-ethylpentyl)amine, N-methylbis(3-ethylpentyl)amine,
N-methylbis(2-propylbutyl)amine, N-methylbis(cycloheptyl)amine,
N-methylbis(methylcyclohexyl)amine
N-methyldibenzylamine, N-methylbis(2-octyl)amine,
N-methylbis(3-octyl)amine
N-methylbis(4-octyl)amine, N-methylbis(2-methylheptyl)amine,
N-methylbis(3-methylheptyl)amine,
N-methylbis(4-methylheptyl)amine,
N-methylbis(5-methylheptyl)amine,
N-methylbis(6-methylheptyl)amine, N-methylbis(2-ethylhexyl)amine,
N-methylbis(3-ethylhexyl)amine, N-methylbis(4-ethylhexyl)amine,
N-methylbis(2-propylpentyl)amine, N-methylbis(cyclooctyl)amine,
N-methylbis(dimethylcyclohexyl)amine, N-ethyldiisopropylamine,
N-ethylbis(2-butyl)amine, N-ethylbis(isobutyl)amine,
N-ethylbis(2-pentyl)amine, N-ethylbis(3-pentyl)amine,
N-ethylbis(2-methylbutyl)amine, N-ethylbis(3-methylbutyl)amine,
N-ethyldicyclopentylamine, N-ethylbis(2-hexyl)amine,
N-ethylbis(3-hexyl)amine, N-ethylbis(2-methylpentyl)amine,
N-ethylbis(3-methylpentyl)amine, N-ethylbis(4-methylpentyl)amine,
N-ethylbis(2-ethylbutyl)amine, N-ethyldicyclohexylamine,
N-ethylbis(2-heptyl)amine, N-ethylbis(3-heptyl)amine,
N-ethylbis(4-heptyl)amine, N-ethylbis(2-methylhexyl)amine,
N-ethylbis(3-methylhexyl)amine, N-ethylbis(4-methylhexyl)amine,
N-ethylbis(5-methylhexyl)amine, N-ethylbis(2-ethylpentyl)amine,
N-ethylbis(3-ethylpentyl)amine, N-ethylbis(2-propylbutyl)amine,
N-ethylbis(cycloheptyl)amine, N-ethylbis(methylcyclohexyl)amine,
N-ethyldi(benzyl)amine, N-ethylbis(2-octyl)amine,
N-ethylbis(3-octyl)amine, N-ethylbis(4-octyl)amine,
N-ethylbis(2-methylheptyl)amine, N-ethylbis(3-methylheptyl)amine,
N-ethylbis(4-methylheptyl)amine, N-ethylbis(5-methylheptyl)amine,
N-ethylbis(6-methylheptyl)amine, N-ethylbis(2-ethylhexyl)amine,
N-ethylbis(3-ethylhexyl)amine, N-ethylbis(4-ethylhexyl)amine,
N-ethylbis(2-propylpentyl)amine, N-ethylbis(cyclooctyl)amine,
N-ethylbis(dimethylcyclohexyl)amine.

Nonlimiting examples of alkali metal tetraphenylborates or alkaline earth metal tetraphenylborates used are:
lithium tetrakis(pentafluorophenyl)borate, sodium tetrakis(pentafluorophenyl)borate, potassium tetrakis(pentafluorophenyl)borate, lithium tetrakis(2,3,4,6-tetrafluorophenyl)borate, sodium tetrakis(2,3,4,6-tetrafluorophenyl)borate, potassium tetrakis(2,3,4,6-tetrafluorophenyl)borate, lithium tetrakis(2,3,5,6-tetrafluorophenyl)borate, sodium tetrakis(2,3,5,6-tetrafluorophenyl)borate, potassium tetrakis(2,3,5,6-tetrafluorophenyl)borate, lithium tetrakis(2,3,5-trifluorophenyl)borate, sodium tetrakis(2,3,5-trifluorophenyl)borate, potassium tetrakis(2,3,5-trifluorophenyl)borate, lithium tetrakis(2,3,6-trifluorophenyl)borate, sodium tetrakis(2,3,6-trifluorophenyl)borate, potassium tetrakis(2,3,6-trifluorophenyl)borate, lithium tetrakis(1,3-difluorophenyl)borate, sodium tetrakis(1,3-difluorophenyl)borate, potassium tetrakis(1,3-difluorophenyl)borate, lithium tetrakis(2,3,5,6-tetrafluoro-4-methylphenyl)borate, sodium tetrakis(2,3,5,6-tetrafluoro-4-methylphenyl)borate, potassium tetrakis(2,3,5,6-tetrafluoro-4-methylphenyl)borate, lithium tetrakis(2,3,4,6-tetrafluoro-5-methylphenyl)borate, sodium tetrakis(2,3,4,6-tetrafluoro-5-methylphenyl)borate, potassium tetrakis(2,3,4,6-tetrafluoro-5-methylphenyl)borate, lithium tetrakis(2,3,5-trifluorophenyl)borate, sodium tetrakis(2,3,5-trifluorophenyl)borate, potassium tetrakis(2,3,5-trifluorophenyl)borate, lithium tetrakis(2,4,5-trifluoro-6-methylphenyl)borate, sodium tetrakis(2,4,5-trifluoro-6-methylphenyl)borate, potassium tetrakis(2,4,5-trifluoro-6-methylphenyl)borate, lithium tetrakis(2,3,6-trifluoro-4-methylphenyl)borate, sodium tetrakis(2,3,6-trifluoro-4-methylphenyl)borate, potassium tetrakis(2,3,6-trifluoro-4-methylphenyl)borate, lithium tetrakis(2,4,6-trifluoro-3-methylphenyl)borate, sodium tetrakis(2,4,6-trifluoro-3-methylphenyl)borate, potassium tetrakis(2,4,6-trifluoro-3-methylphenyl)borate, lithium tetrakis(2,6-difluoro-3-methylphenyl)borate, sodium tetrakis(2,6-difluoro-3-methylphenyl)borate, potassium tetrakis(2,6-difluoro-3-methylphenyl)borate, lithium tetrakis(2,4-difluoro-5-methylphenyl)borate, sodium tetrakis(2,4-difluoro-5-methylphenyl)borate, potassium tetrakis(2,4-difluoro-5-methylphenyl)borate, lithium tetrakis(3,5-difluoro-2-methylphenyl)borate, sodium tetrakis(3,5-difluoro-2-methylphenyl)borate, potassium tetrakis(3,5-difluoro-2-methylphenyl)borate, lithium tetrakis(4-methoxy-2,3,5,6-tetrafluorophenyl)borate, sodium tetrakis(4-methoxy-2,3,5,6-tetrafluorophenyl)borate, potassium tetrakis(4-methoxy-2,3,5,6-tetrafluorophenyl)borate, lithium tetrakis(3-methoxy-2,4,5,6-tetrafluorophenyl)borate, sodium tetrakis(3-methoxy-2,4,5,6-tetrafluorophenyl)borate, potassium tetrakis(3-methoxy-2,4,5,6-tetrafluorophenyl)borate, lithium tetrakis(2-methoxy-3,4,5,6-tetrafluorophenyl)borate, sodium tetrakis(2-methoxy-3,4,5,6-tetrafluorophenyl)borate, potassium tetrakis(2-methoxy-3,4,5,6-tetrafluorophenyl)borate.

These borates can also contain solvents, e.g. etherate or the like. The reaction to form the corresponding ammonium compounds of the formula (I) or (II) can be carried out in an aliphatic or aromatic solvent such as toluene, heptane, tetrahydrofuran or diethyl ether. The reaction time is from 1 minute to 24 hours, with preference being given to a reaction time of from 5 minutes to 240 minutes. The reaction temperature is in the range from −10° C. to +200° C., preferably from 0° C. to 50° C.

The present invention further provides a catalyst system. The catalyst system of the present invention comprises:

A) a least one organometallic transition metal compound,

B) at least one Lewis base,

C) at least one support component and

D) at least one novel compound of the formula (I) or (II).

Organometallic transition metal compounds A) used are, for example, metallocene compounds. These can be, for example, bridged or unbridged biscyclopentadienyl complexes as are described, for example, in EP-A-0 129 368, EP-A-0 561 479, EP-A-0 545 304 and EP-A-0 576 970, monocyclopentadienyl complexes such as bridged amidocyclopentadienyl complexes as described, for example, in EP-A-0 416 815, multinuclear cyclopentadienyl complexes as described, for example, in EP-A-0 632 063, π-ligand-substituted tetrahydropentalenes as described, for example, in EP-A-0 659 758 or π-ligand-substituted tetrahydroindenes as described, for example, in EP-A-0 661 300. It is also possible to use organometallic compounds in which the complexing ligand contains no cyclopentadienyl ligand. Examples of such compounds are diamine complexes of metals of transition groups III and IV of the Periodic Table of the Elements, as are described, for example, by D. H. McConville et al, Macromolecules, 1996, 29, 5241 and D. H. McConville et al, J. Am. Chem. Soc., 1996, 118, 10008. In addition, diimine complexes of metals of transition group VIII of the Periodic Table of the Elements (e.g. $Ni^{2+}$ or $Pd^{2+}$ complexes) as are described by Brookhart et al, J. Am. Chem. Soc. 1995, 117, 6414 and Brookhart et al, J. Am. Chem. Soc., 1996, 118, 267, can also be used. Further compounds which can be used are 2,6-bis(imino)pyridyl complexes of metals of transition group VIII of the Periodic Table of the Elements (e.g. $Co^{2+}$ or $Fe^{2+}$ complexes) as are described by Brookhart et al, J. Am. Chem. Soc. 1998, 120, 4049 and Gibson et al, Chem. Commun. 1998, 849. It is also possible to use metallocene compounds whose complexing ligand contains heterocycles. Examples of such compounds are described in WO 98/22486.

Preferred metallocene compounds are unbridged or bridged compounds of the formula (III),

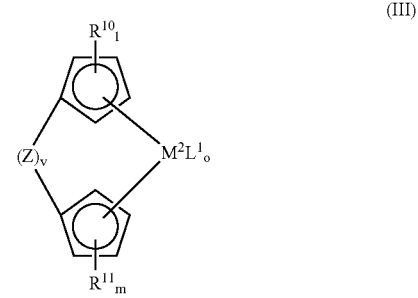

where $M^2$ is a metal of transition group III, IV, V or VI of the Periodic Table of the Elements, in particular Ti, Zr or Hf, $R^{10}$ are identical or different and are each a hydrogen atom or $Si(R^{12})_3$, where $R^{12}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^{10}$ is a $C_1$–$C_{30}$ group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^{10}$ may be connected to one another in such a way that the radicals $R^{10}$ and the atoms of the cyclopentadienyl ring which connect them form a $C_4$–$C_{24}$ ring system which may in turn be substituted, $R^{11}$ are identical or different and are each a hydrogen atom or $Si(R^{12})_3$, where $R^{12}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^{11}$ is a $C_1$–$C_{30}$ group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_5$–$C_{24}$-alkylheteroaryl, $C_5$–$C_{24}$-alkylheteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^{11}$ may be connected to one another in such a way that the radicals $R^{11}$ and the atoms of the cyclopentadienyl ring which connect them form a $C_4$–$C_{24}$ ring system which may in turn be substituted, l is 5 when v=0, and l is 4 when v=1, m is 5 when v=0, and m is 4 when v=1, $L^1$ may be identical or different and are each a hydrogen atom, a $C_1$–$C_{10}$-hydrocarbon group such as $C_1$–$C_{10}$-alkyl or $C_6$–$C_{10}$-aryl, a halogen atom or $OR^{16}$, $SR^{16}$, $OSi(R^{16})_3$, $Si(R^{16})_3$, $P(R^{16})_2$ or $N(R^{16})_2$, where $R^{16}$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or $L^1$ is a toluenesulfonyl, trifluoroacetyl, trifluoroacetoxyl, trifluoromethanesulfonyl, nonafluorobutanesulfonyl or 2,2,2-trifluoroethanesulfonyl group, o is an integer from 1 to 4, preferably 2, z is a bridging structural element between the two cyclopentadienyl rings and v is 0 or 1.

Examples of Z are $M^2R^{13}R^{14}$ groups, where $M^2$ is carbon, silicon, germanium, boron or tin and $R^{13}$ and $R^{14}$ are identical or different and are each a $C_1$–$C_{20}$-hydrocarbon-containing group such as $C_1$–$C_{10}$-alkyl, $C_6$–$C_{14}$-aryl or trimethylsilyl. Z is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$. It is also possible for Z together with one or more radicals $R^{10}$ and/or $R^{11}$ to form a monocyclic or polycyclic ring system.

Preference is given to chiral bridged metallocene compounds of the formula (III), particularly ones in which v is equal to 1 and one or both cyclopentadienyl rings are substituted so that they form an indenyl ring. The indenyl ring is preferably substituted, in particular in the 2 position, 4 position, 2,4,5 positions, 2,4,6 positions, 2,4,7 positions or 2,4,5,6 positions, by $C_1$–$C_{20}$ groups such as $C_1$–$C_{10}$-alkyl or $C_6$–$C_{20}$-aryl, where two or more substituents on the indenyl ring may also together form a ring system.

Chiral bridged metallocene compounds of the formula (III) can be used as pure racemic or pure meso compounds. However, it is also possible to use mixtures of a racemic compound and a meso compound.

Examples of metallocene compounds are:
dimethylsilanediylbis(indenyl)zirconium dichloride
dimethylsilanediylbis(4-naphthylindenyl)zirconium dichloride
dimethylsilanediylbis(2-methylbenzoindenyl)zirconium dichloride
dimethylsilanediylbis(2-methylindenyl)zirconium dichloride
dimethylsilanediylbis(2-methyl-4-(1-naphthyl)indenyl)zirconium dichloride
dimethylsilanediylbis(2-methyl-4-(2-naphthyl)indenyl)zirconium dichloride
dimethylsilanediylbis(2-methyl-4-phenylindenyl)zirconium dichloride
dimethylsilanediylbis(2-methyl-4-tert-butylindenyl)zirconium dichloride
dimethylsilanediylbis(2-methyl-4-isopropylindenyl)zirconium dichloride
dimethylsilanediylbis(2-methyl-4-ethylindenyl)zirconium dichloride
dimethylsilanediylbis(2-methyl-4-α-acenaphthindenyl)zirconium dichloride
dimethylsilanediylbis(2,4-dimethylindenyl)zirconium dichloride
dimethylsilanediylbis(2-ethylindenyl)zirconium dichloride
dimethylsilanediylbis(2-ethyl-4-ethylindenyl)zirconium dichloride
dimethylsilanediylbis(2-ethyl-4-phenylindenyl)zirconium dichloride
dimethylsilanediylbis(2-methyl-4,5-benzoindenyl)zirconium dichloride
dimethylsilanediylbis(2-methyl-4,6-diisopropylindenyl)zirconium dichloride
dimethylsilanediylbis(2-methyl-4,5-diisopropylindenyl)zirconium dichloride
dimethylsilanediylbis(2,4,6-trimethylindenyl)zirconium dichloride
dimethylsilanediylbis(2,5,6-trimethylindenyl)zirconium dichloride
dimethylsilanediylbis(2,4,7-trimethylindenyl)zirconium dichloride
dimethylsilanediylbis(2-methyl-5-isobutylindenyl)zirconium dichloride
dimethylsilanediylbis(2-methyl-5-tert-butylindenyl)zirconium dichloride
methyl(phenyl)silanediylbis(2-methyl-4-phenylindenyl)zirconium dichloride
methyl(phenyl)silanediylbis(2-methyl-4,6-diisopropylindenyl)-zirconium dichloride
methyl(phenyl)silanediylbis(2-methyl-4-isopropylindenyl)-zirconium dichloride
methyl(phenyl)silanediylbis(2-methyl-4,5-benzoindenyl) zirconium dichloride
methyl(phenyl)silanediylbis(2-methyl-4,5-(methylbenzo)indenyl)-zirconium dichloride
methyl(phenyl)silanediylbis(2-methyl-4,5-(tetramethylbenzo)-indenyl)-zirconium dichloride
methyl(phenyl)silanediylbis(2-methyl-4-α-acenaphthindenyl)-zirconium dichloride
methyl(phenyl)silanediylbis(2-methylindenyl)zirconium dichloride
methyl(phenyl)silanediylbis(2-methyl-5-isobutylindenyl) zirconium dichloride
1,2-ethanediylbis(2-methyl-4-phenylindenyl)zirconium dichloride
1,4-butanediylbis(2-methyl-4-phenylindenyl)zirconium dichloride
1,2-ethanediylbis(2-methyl-4,6-diisopropylindenyl)zirconium dichloride
1,4-butanediylbis(2-methyl-4-isopropylindenyl)zirconium dichloride
1,4-butanediylbis(2-methyl-4,5-benzoindenyl)zirconium dichloride
1,2-ethanediylbis(2-methyl-4,5-benzoindenyl)zirconium dichloride
1,2-ethanediylbis(2,4,7-trimethylindenyl)zirconium dichloride
1,2-ethanediylbis(2-methylindenyl)zirconium dichloride
1,4-butanediylbis(2-methylindenyl)zirconium dichloride
[4-($\eta^5$-cyclopentadienyl)-4,6,6-trimethyl($\eta^5$-4,5-tetrahydropentalene)]dichlorozirconium
[4-($\eta^5$-3'-trimethylsilylcyclopentadienyl)-4,6,6-trimethyl ($\eta^5$-4,5-tetrahydropentalene)]dichlorozirconium
[4-($\eta^5$-3'-isopropylcyclopentadienyl)-4,6,6-trimethyl($\eta^5$-4,5-tetrahydropentalene)]dichlorozirconium
[4-($\eta^5$-cyclopentadienyl)-4,7,7-trimethyl($\eta^5$-4,5,6,7-tetrahydroindenyl)]dichlorotitanium
[4-($\eta^5$-cyclopentadienyl)-4,7,7-trimethyl($\eta^5$-4,5,6,7-tetrahydroindenyl)]dichlorozirconium
[4-($\eta^5$-cyclopentadienyl)-4,7,7-trimethyl($\eta^5$-4,5,6,7-tetrahydroindenyl)]dichlorohafnium
[4-($\eta^5$-3'-tert-butylcyclopentadienyl)-4,7,7-trimethyl ($\eta^5$-4,5,6,7-tetrahydroindenyl)]dichlorotitanium
4-($\eta^5$-3'-isopropylcyclopentadienyl)-4,7,7-trimethyl($\eta^5$-4,5,6,7-tetrahydroindenyl)]dichlorotitanium
4-($\eta^5$-3'-methylcyclopentadienyl)-4,7,7-trimethyl($\eta^5$-4,5,6,7-tetrahydroindenyl)]dichlorotitanium
4-($\eta^5$-3'-trimethylsilylcyclopentadienyl)-2-trimethylsilyl-4,7,7-trimethyl($\eta^5$-4,5,6,7-tetrahydroindenyl)]dichlorotitanium
4-($\eta^5$-3'-tert-butylcyclopentadienyl)-4,7,7-trimethyl($\eta^5$-4,5,6,7-tetrahydroindenyl)]dichlorozirconium
(tert-butylamido)(tetramethyl-$\eta^5$-cyclopentadienyl)dimethylsilyl-dichlorotitanium
(tert-butylamido)(tetramethyl-$\eta^5$-cyclopentadienyl)-1,2-ethane-diyldichlorotitanium
(methylamido)(tetramethyl-$\eta^5$-cyclopentadienyl)dimethylsilyl-dichlorotitanium
(methylamido)(tetramethyl-$\eta^5$-cyclopentadienyl)-1,2-ethanediyl-dichlorotitanium (tert-butylamido)(2,4-dimethyl-2,4-pentadien-1-yl)dimethylsilyl-dichlorotitanium
bis(cyclopentadienyl)zirconium dichloride
bis(n-butylcyclopentadienyl)zirconium dichloride
bis(1,3-dimethylcyclopentadienyl)zirconium dichloride
tetrachloro[1-[bis($\eta^5$-1H-inden-1-ylidene)methylsilyl]-3-$\eta^5$ penta-2,4-dien-1-ylidene)-3-$\eta^5$-9H-fluoren-9-ylidene)butane]-dizirconium
tetrachloro[2-[bis($\eta^5$-2-methyl-1H-inden-1-ylidene)methoxysilyl]-5-($\eta^5$-2,3,4,5-tetramethylcyclopenta-2,4-dien-1-ylidene)-5-($\eta^5$-9H-fluoren-9-ylidene)hexane]dizirconium
tetrachloro[1-[bis($\eta^5$-1H-inden-1-ylidene)methylsilyl]-6-(5-cyclopenta-2,4-dien-1-ylidene)-6-($\eta^5$-9H-fluoren-9-ylidene)-3-oxaheptane]dizirconium
dimethylsilanediylbis(2-methyl-4-(tert-butylphenyl)indenyl)-zirconium dichloride
dimethylsilanediylbis(2-methyl-4-(4-methylphenyl)indenyl)]-zirconium dichloride
dimethylsilanediylbis(2-methyl-4-(4-ethylphenyl)indenyl)]-zirconium dichloride
dimethylsilanediylbis(2-methyl-4-(4-trifluoromethylphenyl)-indenyl)]zirconium dichloride
dimethylsilanediylbis(2-methyl-4-(4-methoxyphenyl)indenyl)]-zirconium dichloride
dimethylsilanediylbis(2-ethyl-4-(4-tert-butylphenyl)indenyl)]-zirconium dichloride
dimethylsilanediylbis(2-ethyl-4-(4-methylphenyl)indenyl) zirconium dichloride
dimethylsilanediylbis(2-ethyl-4-(4-ethylphenyl)indenyl)zirconium dichloride
dimethylsilanediylbis(2-ethyl-4-(4-trifluoromethylphenyl)-indenyl)-zirconium dichloride
dimethylsilanediylbis(2-ethyl-4-(4-methoxyphenyl)indenyl)-zirconium dichloride
dimethylsilanediylbis(2-methyl-4-(4-tert-butylphenyl)indenyl)-dimethylzirconium
dimethylsilanediylbis(2-methyl-4-(4-methylphenyl)indenyl)-dimethyl-zirconium
dimethylsilanediylbis(2-methyl-4-(4-ethylphenyl)indenyl) dimethyl-zirconium
dimethylsilanediylbis(2-methyl-4-(4-trifluoromethylphenyl)-indenyl)dimethylzirconium
dimethylsilanediylbis(2-methyl-4-(4-methoxyphenylindenyl)-dimethylzirconium
dimethylsilanediylbis(2-ethyl-4-(4-tert-butylphenylindenyl)-dimethylzirconium
dimethylsilanediylbis(2-ethyl-4-(4-methylphenylindenyl) dimethyl-zirconium
dimethylsilanediylbis(2-ethyl-4-(4-ethylphenylindenyl)diethyl-zirconium
dimethylsilanediylbis(2-ethyl-4-(4-trifluoromethylphenyl-indenyl)-dimethylzirconium
dimethylsilanediylbis(2-ethyl-4-(4-methoxyphenylindenyl) dimethyl-zirconium
dimethylsilanediylbis(2-methyl-4-(4'-tert-butylphenyl)indenyl)-zirconium dichloride
dimethylsilanediylbis(2-methyl-4-(4'-tert-butylphenyl)indenyl)-hafnium dichloride
dimethylsilanediylbis(2-methyl-4-(4'-tert-butylphenyl)indenyl)-titanium dichloride
dimethylsilanediylbis(2-methyl-4-(4'-methylphenyl)indenyl)-zirconium dichloride
dimethylsilanediylbis(2-methyl-4-(4'-n-propylphenyl)indenyl)-zirconium dichloride
dimethylsilanediylbis(2-methyl-4-(4'-n-butylphenyl)indenyl)-zirconium dichloride
dimethylsilanediylbis(2-methyl-4-(4'-hexylphenyl)indenyl)-zirconium dichloride
dimethylsilanediylbis(2-methyl-4-(4'-sec-butylphenyl)indenyl)-zirconium dichloride
dimethylsilanediylbis(2-ethyl-4-phenylindenyl)zirconium dichloride
dimethylsilanediylbis(2-ethyl-4-(4'-methylphenyl)indenyl)-zirconium dichloride
dimethylsilanediylbis(2-ethyl-4-(4'-ethylphenyl)indenyl) zirconium dichloride
dimethylsilanediylbis(2-ethyl-4-(4'-n-propylphenyl)indenyl)-zirconium dichloride
dimethylsilanediylbis(2-ethyl-4-(4'-n-butylphenyl)indenyl)-zirconium dichloride
dimethylsilanediylbis(2-ethyl-4-(4'-hexylphenyl)indenyl)-zirconium dichloride
dimethylsilanediylbis(2-ethyl-4-(4'-pentylphenyl)indenyl)-zirconium dichloride
dimethylsilanediylbis(2-ethyl-4-(4'-cyclohexylphenyl)indenyl)-zirconium dichloride
dimethylsilanediylbis(2-ethyl-4-(4'-sec-butylphenyl)indenyl)-zirconium dichloride
dimethylsilanediylbis(2-ethyl-4-(4'-tert-butylphenyl)indenyl)-zirconium dichloride
dimethylsilanediylbis(2-n-propyl-4-phenyl)indenyl)zirconium dichloride
dimethylsilanediylbis(2-n-propyl-4-(4'-methylphenyl)indenyl)-zirconium dichloride
dimethylsilanediylbis(2-n-propyl-4-(4'-ethylphenyl)indenyl)-zirconium dichloride
dimethylsilanediylbis(2-n-propyl-4-(4'-isopropylphenyl)indenyl)-zirconium dichloride
dimethylsilanediylbis(2-n-propyl-4-(4'-n-butylphenyl)indenyl)-zirconium dichloride
dimethylsilanediylbis(2-n-propyl-4-(4'-hexylphenyl)indenyl)-zirconium dichloride
dimethylsilanediylbis(2-n-propyl-4-(4'-cyclohexylphenyl) indenyl)-zirconium dichloride
dimethylsilanediylbis(2-n-propyl-4-(4'-sec-butylphenyl)indenyl)-zirconium dichloride
dimethylsilanediylbis(2-n-propyl-4-(4'-tert-butylphenyl)indenyl)-zirconium dichloride
dimethylsilanediylbis(2-n-butyl-4-phenyl)indenyl)zirconium dichloride
dimethylsilanediylbis(2-n-butyl-4-(4'-methylphenyl)indenyl)-zirconium dichloride
dimethylsilanediylbis(2-n-butyl-4-(4'-ethylphenyl)indenyl)-zirconium dichloride
dimethylsilanediylbis(2-n-butyl-4-(4'-n-propylphenyl)indenyl)-zirconium dichloride
dimethylsilanediylbis(2-n-butyl-4-(4'-isopropylphenyl)indenyl)-zirconium dichloride
dimethylsilanediylbis(2-n-butyl-4-(4'-n-butylphenyl)indenyl)-zirconium dichloride
dimethylsilanediylbis(2-n-butyl-4-(4'-hexylphenyl)indenyl)-zirconium dichloride
dimethylsilanediylbis(2-n-butyl-4-(4'-cyclohexylphenyl)indenyl)-zirconium dichloride
dimethylsilanediylbis(2-n-butyl-4-(4'-sec-butylphenyl)indenyl)-zirconium dichloride
dimethylsilanediylbis(2-n-butyl-4-(4'-tert-butylphenyl)indenyl)-zirconium dichloride
dimethylsilanediylbis(2-hexyl-4-phenylindenyl)zirconium dichloride
dimethylsilanediylbis(2-hexyl-4-(4'-methylphenyl)indenyl)-zirconium dichloride dimethylsilanediylbis(2-hexyl-4-(4'-ethylphenyl)indenyl)zirconium dichloride
dimethylsilanediylbis(2-hexyl-4-(4'-n-propylphenyl)indenyl)-zirconium dichloride
dimethylsilanediylbis(2-hexyl-4-(4'-isopropylphenyl)indenyl)-zirconium dichloride
dimethylsilanediylbis(2-hexyl-4-(4'-n-butylphenyl)indenyl)-zirconium dichloride
dimethylsilanediylbis(2-hexyl-4-(4'-hexylphenyl)indenyl)zirconium dichloride
dimethylsilanediylbis(2-hexyl-4-(4'-cyclohexylphenyl)indenyl)-zirconium dichloride
dimethylsilanediylbis(2-hexyl-4-(4'-sec-butylphenyl)indenyl)-zirconium dichloride
dimethylsilanediylbis(2-hexyl-4-(4'-tert-butylphenyl)indenyl)-zirconium dichloride
dimethylsilanediylbis(2-methyl-4-(4'-tert-butylphenyl)indenyl)-zirconium bis(dimethylamide)
dimethylsilanediylbis(2-ethyl-4-(4'-tert-butylphenyl)indenyl)-dibenzylzirconium
dimethylsilanediylbis(2-methyl-4-(4'-tert-butylphenyl)indenyl)-dimethylzirconium
dimethylgermanediylbis(2-ethyl-4-(4'-tert-butylphenyl)indenyl)-zirconium dichloride
dimethylgermanediylbis(2-ethyl-4-(4'-tert-butylphenyl)indenyl)-hafnium dichloride
dimethylgermanediylbis(2-propyl-4-(4'-tert-butylphenyl)indenyl)-titanium dichloride
dimethylgermanediylbis(2-methyl-4-(4'-tert-butylphenyl)indenyl)-zirconium dichloride
ethylidenebis(2-ethyl-4-phenylindenyl)zirconium dichloride
ethylidenebis(2-ethyl-4-(4'-tert-butylphenyl)indenyl)zirconium dichloride
ethylidenebis(2-n-propyl-4-(4'-tert-butylphenyl)indenyl)zirconium dichloride
ethylidenebis(2-n-butyl-4-(4'-tert-butylphenyl)indenyl)titanium dichloride
ethylidenebis(2-hexyl-4-(4'-tert-butylphenyl)indenyl)dibenzyl-zirconium
ethylidenebis(2-ethyl-4-(4'-tert-butylphenyl)indenyl)dibenzyl-hafnium
ethylidenebis(2-methyl-4-(4'-tert-butylphenyl)indenyl)dibenzyl-titanium
ethylidenebis(2-methyl-4-(4'-tert-butylphenyl)indenyl)zirconium dichloride
ethylidenebis(2-ethyl-4-(4'-tert-butylphenyl)indenyl)dimethyl-hafnium
ethylidenebis(2-n-propyl-4-phenylindenyl)dimethyltitanium
ethylidenebis(2-ethyl-4-(4'-tert-butylphenyl)indenyl)zirconium bis(dimethylamide)
ethylidenebis(2-ethyl-4-(4'-tert-butylphenyl)indenyl)hafnium bis(dimethylamide)
ethylidenebis(2-ethyl-4-(4'-tert-butylphenyl)indenyl)titanium bis(dimethylamide)
methylethylidenebis(2-ethyl-4-(4'-tert-butylphenyl)indenyl)-zirconium dichloride
methylethylidenebis(2-ethyl-4-(4'-tert-butylphenyl)indenyl)-hafnium dichloride
phenylphosphinediyl(2-ethyl-4-(4'-tert-butylphenyl)indenyl)-zirconium dichloride
phenylphosphinediyl(2-methyl-4-(4'-tert-butylphenyl)indenyl)-zirconium dichloride
dimethylsilanediyl(2-methyl-4-azapentalene)(2-methyl-4-(4'-methylphenylindenyl)zirconium dichloride
dimethylsilanediyl(2-methyl-5-azapentalene)(2-methyl-4-(4'-methylphenylindenyl)zirconium dichloride
dimethylsilanediyl(2-methyl-6-azapentalene)(2-methyl-4-(4'-methylphenylindenyl)zirconium dichloride
dimethylsilanediyl(2-methyl-N-phenyl-4-azapentalene)(2-methyl-4-(4'-methylphenyl)indenyl)zirconium dichloride
dimethylsilanediyl(2-methyl-N-phenyl-5-azapentalene)(2-methyl-4-(4'-methylphenyl)indenyl)zirconium dichloride
dimethylsilanediyl(2-methyl-N-phenyl-6-azapentalene)(2-methyl-4-(4'-methylphenyl)indenyl)zirconium dichloride
dimethylsilanediyl(2,5-dimethyl-4-azapentalene)(2-methyl-4-(4'-methylphenyl)indenyl)zirconium dichloride
dimethylsilanediyl(2,5-dimethyl-6-azapentalene)(2-methyl-4-(4'-methylphenyl)indenyl)zirconium dichloride
dimethylsilanediyl(2,5-dimethyl-N-phenyl-4-azapentalene)(2-methyl-4-(4'-methylphenyl)indenyl)zirconium dichloride
dimethylsilanediyl(2,5-dimethyl-N-phenyl-6-azapentalene)(2-methyl-4-(4'-methylphenyl)indenyl)zirconium dichloride
dimethylsilanediyl(2-methyl-4-thiapentalene)(2-methyl-4-(4'-methylphenyl)indenyl)zirconium dichloride
dimethylsilanediyl(2-methyl-5-thiapentalene)(2-methyl-4-(4'-methylphenyl)indenyl)zirconium dichloride
dimethylsilanediyl(2-methyl-6-thiapentalene)(2-methyl-4-(4'-methylphenyl)indenyl)zirconium dichloride
dimethylsilanediyl(2,5-dimethyl-4-thiapentalene)(2-methyl-4-(4'-methylphenyl)indenyl)zirconium dichloride
dimethylsilanediyl(2,5-dimethyl-6-thiapentalene)(2-methyl-4-(4'-methylphenyl)indenyl)zirconium dichloride
dimethylsilanediyl(2-methyl-4-oxapentalene)(2-methyl-4-(4'-methylphenyl)indenyl)zirconium dichloride
dimethylsilanediyl(2-methyl-5-oxapentalene)(2-methyl-4-(4'-methylphenyl)indenyl)zirconium dichloride
dimethylsilanediyl(2-methyl-6-oxapentalene)(2-methyl-4-(4'-methylphenyl)indenyl)zirconium dichloride
dimethylsilanediyl(2,5-dimethyl-4-oxapentalene)(2-methyl-4-(4'-methylphenyl)indenyl)zirconium dichloride
dimethylsilanediyl(2,5-dimethyl-6-oxapentalene)(2-methyl-4-(4'-methylphenyl)indenyl)zirconium dichloride
dimethylsilanediyl(2-methyl-4-azapentalene)(2-methyl-4-(4'-ethylphenyl)indenyl)zirconium dichloride
dimethylsilanediyl(2-methyl-5-azapentalene)(2-methyl-4-(4'-ethylphenyl)indenyl)zirconium dichloride
dimethylsilanediyl(2-methyl-6-azapentalene)(2-methyl-4-(4'-ethylphenyl)indenyl)zirconium dichloride
dimethylsilanediyl(2-methyl-N-phenyl-4-azapentalene)(2-methyl-4-(4'-ethylphenyl)indenyl)zirconium dichloride
dimethylsilanediyl(2-methyl-N-phenyl-5-azapentalene)(2-methyl-4-(4'-ethylphenyl)indenyl)zirconium dichloride
dimethylsilanediyl(2-methyl-N-phenyl-6-azapentalene)(2-methyl-4-(4'-ethylphenyl)indenyl)zirconium dichloride
dimethylsilanediyl(2,5-dimethyl-4-azapentalene)(2-methyl-4-(4'-ethylphenyl)indenyl)zirconium dichloride
dimethylsilanediyl(2,5-dimethyl-6-azapentalene)(2-methyl-4-(4'-ethylphenyl)indenyl)zirconium dichloride
dimethylsilanediyl(2,5-dimethyl-N-phenyl-4-azapentalene)(2-methyl-4-(4'-ethylphenyl)indenyl)zirconium dichloride
dimethylsilanediyl(2,5-dimethyl-N-phenyl-6-azapentalene)(2-methyl-4-(4'-ethylphenyl)indenyl)zirconium dichloride
dimethylsilanediyl(2-methyl-4-thiapentalene)(2-methyl-4-(4'-ethylphenyl)indenyl)zirconium dichloride
dimethylsilanediyl(2-methyl-5-thiapentalene)(2-methyl-4-(4'-ethylphenyl)indenyl)zirconium dichloride dimethylsilanediyl(2-methyl-6-thiapentalene)(2-methyl-4-(4'-ethylphenyl)indenyl)zirconium dichloride
dimethylsilanediyl(2,5-dimethyl-4-thiapentalene)(2-methyl-4-(4'-ethylphenyl)indenyl)zirconium dichloride
dimethylsilanediyl(2,5-dimethyl-6-thiapentalene)(2-methyl-4-(4'-ethylphenyl)indenyl)zirconium dichloride
dimethylsilanediyl(2-methyl-4-oxapentalene)(2-methyl-4-(4'-ethylphenyl)indenyl)zirconium dichloride
dimethylsilanediyl(2-methyl-5-oxapentalene)(2-methyl-4-(4'-ethylphenyl)indenyl)zirconium dichloride
dimethylsilanediyl(2-methyl-6-oxapentalene)(2-methyl-4-(4'-ethylphenyl)indenyl)zirconium dichloride
dimethylsilanediyl(2,5-dimethyl-4-oxapentalene)(2-methyl-4-(4'-ethylphenyl)indenyl)zirconium dichloride
dimethylsilanediyl(2,5-dimethyl-6-oxapentalene)(2-methyl-4-(4'-ethylphenyl)indenyl)zirconium dichloride
dimethylsilanediyl(2-methyl-4-azapentalene)(2-methyl-4-(4'-n-propylphenyl)indenyl)zirconium dichloride
dimethylsilanediyl(2-methyl-5-azapentalene)(2-methyl-4-(4'-n-propylphenyl)indenyl)zirconium dichloride
dimethylsilanediyl(2-methyl-6-azapentalene)(2-methyl-4-(4'-n-propylphenyl)indenyl)zirconium dichloride
dimethylsilanediyl(2-methyl-N-phenyl-4-azapentalene)(2-methyl-4-(4'-n-propylphenyl)indenyl)zirconium dichloride
dimethylsilanediyl(2-methyl-N-phenyl-5-azapentalene)(2-methyl-4-(4'-n-propylphenyl)indenyl)zirconium dichloride
dimethylsilanediyl(2-methyl-N-phenyl-6-azapentalene)(2-methyl-4-(4'-n-propylphenyl)indenyl)zirconium dichloride
dimethylsilanediyl(2,5-dimethyl-4-azapentalene)(2-methyl-4-(4'-n-propylphenyl)indenyl)zirconium dichloride
dimethylsilanediyl(2,5-dimethyl-6-azapentalene)(2-methyl-4-(4'-n-propylphenyl)indenyl)zirconium dichloride
dimethylsilanediyl(2,5-dimethyl-N-phenyl-4-azapentalene)(2-methyl-4-(4'-n-propylphenyl)indenyl)zirconium dichloride
dimethylsilanediyl(2,5-dimethyl-N-phenyl-6-azapentalene)(2-methyl-4-(4'-n-propylphenyl)indenyl)zirconium dichloride
dimethylsilanediyl(2-methyl-4-thiapentalene)(2-methyl-4-(4'-n-propylphenyl)indenyl)zirconium dichloride
dimethylsilanediyl(2-methyl-5-thiapentalene)(2-methyl-4-(4'-n-propylphenyl)indenyl)zirconium dichloride
dimethylsilanediyl(2-methyl-6-thiapentalene)(2-methyl-4-(4'-n-propylphenyl)indenyl)zirconium dichloride
dimethylsilanediyl(2,5-dimethyl-4-thiapentalene)(2-methyl-4-(4'-n-propylphenyl)indenyl)zirconium dichloride
dimethylsilanediyl(2,5-dimethyl-6-thiapentalene)(2-methyl-4-(4'-n-propylphenyl)indenyl)zirconium dichloride
dimethylsilanediyl(2-methyl-4-oxapentalene)(2-methyl-4-(4'-n-propylphenyl)indenyl)zirconium dichloride
dimethylsilanediyl(2-methyl-5-oxapentalene)(2-methyl-4-(4'-n-propylphenyl)indenyl)zirconium dichloride
dimethylsilanediyl(2-methyl-6-oxapentalene)(2-methyl-4-(4'-n-propylphenyl)indenyl)zirconium dichloride
dimethylsilanediyl(2,5-dimethyl-4-oxapentalene)(2-methyl-4-(4'-n-propylphenyl)indenyl)zirconium dichloride
dimethylsilanediyl(2,5-dimethyl-6-oxapentalene)(2-methyl-4-(4'-n-propylphenyl)indenyl)zirconium dichloride
dimethylsilanediyl(2-methyl-4-azapentalene)(2-methyl-4-(4'-isopropylphenyl)indenyl)zirconium dichloride
dimethylsilanediyl(2-methyl-5-azapentalene)(2-methyl-4-(4'-isopropylphenyl)indenyl)zirconium dichloride
dimethylsilanediyl(2-methyl-6-azapentalene)(2-methyl-4-(4'-isopropylphenyl)indenyl)zirconium dichloride
dimethylsilanediyl(2-methyl-N-phenyl-4-azapentalene)(2-methyl-4-(4'-isopropylphenyl)indenyl)zirconium dichloride
dimethylsilanediyl(2-methyl-N-phenyl-5-azapentalene)(2-methyl-4-(4'-isopropylphenyl)indenyl)zirconium dichloride dimethylsilanediyl(2-methyl-N-phenyl-6-azapentalene)(2-methyl-4-(4'-isopropylphenyl)indenyl)zirconium dichloride
dimethylsilanediyl(2,5-dimethyl-4-azapentalene)(2-methyl-4-(4'-isopropylphenyl)indenyl)zirconium dichloride
dimethylsilanediyl(2,5-dimethyl-6-azapentalene)(2-methyl-4-(4'-isopropylphenyl)indenyl)zirconium dichloride
dimethylsilanediyl(2,5-dimethyl-N-phenyl-4-azapentalene)(2-methyl-4-(4'-isopropylphenyl)indenyl)zirconium dichloride
dimethylsilanediyl(2,5-dimethyl-N-phenyl-6-azapentalene)(2-methyl-4-(4'-isopropylphenyl)indenyl)zirconium dichloride
dimethylsilanediyl(2-methyl-4-thiapentalene)(2-methyl-4-(4'-isopropylphenyl)indenyl)zirconium dichloride
dimethylsilanediyl(2-methyl-5-thiapentalene)(2-methyl-4-(4'-isopropylphenyl)indenyl)zirconium dichloride
dimethylsilanediyl(2-methyl-6-thiapentalene)(2-methyl-4-(4'-isopropylphenyl)indenyl)zirconium dichloride
dimethylsilanediyl(2,5-dimethyl-4-thiapentalene)(2-methyl-4-(4'-isopropylphenyl)indenyl)zirconium dichloride
dimethylsilanediyl(2,5-dimethyl-6-thiapentalene)(2-methyl-4-(4'-isopropylphenyl)indenyl)zirconium dichloride
dimethylsilanediyl(2-methyl-4-oxapentalene)(2-methyl-4-(4'-isopropylphenyl)indenyl)zirconium dichloride
dimethylsilanediyl(2-methyl-5-oxapentalene)(2-methyl-4-(4'-isopropylphenyl)indenyl)zirconium dichloride
dimethylsilanediyl(2-methyl-6-oxapentalene)(2-methyl-4-(4'-isopropylphenyl)indenyl)zirconium dichloride
dimethylsilanediyl(2,5-dimethyl-4-oxapentalene)(2-methyl-4-(4'-isopropylphenyl)indenyl)zirconium dichloride
dimethylsilanediyl(2,5-dimethyl-6-oxapentalene)(2-methyl-4-(4'-isopropylphenyl)indenyl)zirconium dichloride
dimethylsilanediyl(2-methyl-4-azapentalene)(2-methyl-4-(4'-n-butylphenyl)indenyl)zirconium dichloride
dimethylsilanediyl(2-methyl-5-azapentalene)(2-methyl-4-(4'-n-butylphenyl)indenyl)zirconium dichloride
dimethylsilanediyl(2-methyl-6-azapentalene)(2-methyl-4-(4'-n-butylphenyl)indenyl)zirconium dichloride
dimethylsilanediyl(2-methyl-N-phenyl-4-azapentalene)(2-methyl-4-(4'-n-butylphenyl)indenyl)zirconium dichloride
dimethylsilanediyl(2-methyl-N-phenyl-5-azapentalene)(2-methyl-4-(4'-n-butylphenyl)indenyl)zirconium dichloride
dimethylsilanediyl(2-methyl-N-phenyl-6-azapentalene)(2-methyl-4-(4'-n-butylphenyl)indenyl)zirconium dichloride
dimethylsilanediyl(2,5-dimethyl-4-azapentalene)(2-methyl-4-(4'-n-butylphenyl)indenyl)zirconium dichloride
dimethylsilanediyl(2,5-dimethyl-6-azapentalene)(2-methyl-4-(4'-n-butylphenyl)indenyl)zirconium dichloride
dimethylsilanediyl(2,5-dimethyl-N-phenyl-4-azapentalene)(2-methyl-4-(4'-n-butylphenyl)indenyl)zirconium dichloride
dimethylsilanediyl(2,5-dimethyl-N-phenyl-6-azapentalene)(2-methyl-4-(4'-n-butylphenyl)indenyl)zirconium dichloride
dimethylsilanediyl(2-methyl-4-thiapentalene)(2-methyl-4-(4'-n-butylphenyl)indenyl)zirconium dichloride
dimethylsilanediyl(2-methyl-5-thiapentalene)(2-methyl-4-(4'-n-butylphenyl)indenyl)zirconium dichloride
dimethylsilanediyl(2-methyl-6-thiapentalene)(2-methyl-4-(4'-n-butylphenyl)indenyl)zirconium dichloride dimethylsilanediyl(2,5-dimethyl-4-thiapentalene)(2-methyl-4-(4'-n-butylphenyl)indenyl)zirconium dichloride
dimethylsilanediyl(2,5-dimethyl-6-thiapentalene)(2-methyl-4-(4'-n-butylphenyl)indenyl)zirconium dichloride
dimethylsilanediyl(2-methyl-4-oxapentalene)(2-methyl-4-(4'-n-butylphenyl)indenyl)zirconium dichloride
dimethylsilanediyl(2-methyl-5-oxapentalene)(2-methyl-4-(4'-n-butylphenyl)indenyl)zirconium dichloride
dimethylsilanediyl(2-methyl-6-oxapentalene)(2-methyl-4-(4'-n-butylphenyl)indenyl)zirconium dichloride
dimethylsilanediyl(2,5-dimethyl-4-oxapentalene)(2-methyl-4-(4'-n-butylphenyl)indenyl)zirconium dichloride
dimethylsilanediyl(2,5-dimethyl-6-oxapentalene)(2-methyl-4-(4'-n-butylphenyl)indenyl)zirconium dichloride
dimethylsilanediyl(2-methyl-4-azapentalene)(2-methyl-4-(4'-sec-butylphenyl)indenyl)zirconium dichloride
dimethylsilanediyl(2-methyl-5-azapentalene)(2-methyl-4-(4'-sec-butylphenyl)indenyl)zirconium dichloride
dimethylsilanediyl(2-methyl-6-azapentalene)(2-methyl-4-(4'-sec-butylphenyl)indenyl)zirconium dichloride
dimethylsilanediyl(2-methyl-N-phenyl-4-azapentalene)(2-methyl-4-(4'-sec-butylphenyl)indenyl)zirconium dichloride
dimethylsilanediyl(2-methyl-N-phenyl-5-azapentalene)(2-methyl-4-(4'-sec-butylphenyl)indenyl)zirconium dichloride
dimethylsilanediyl(2-methyl-N-phenyl-6-azapentalene)(2-methyl-4-(4'-sec-butylphenyl)indenyl)zirconium dichloride
dimethylsilanediyl(2,5-dimethyl-4-azapentalene)(2-methyl-4-(4'-sec-butylphenyl)indenyl)zirconium dichloride
dimethylsilanediyl(2,5-dimethyl-6-azapentalene)(2-methyl-4-(4'-sec-butylphenyl)indenyl)zirconium dichloride
dimethylsilanediyl(2,5-dimethyl-N-phenyl-4-azapentalene)(2-methyl-4-(4'-s-butylphenyl)indenyl)zirconium dichloride
dimethylsilanediyl(2,5-dimethyl-N-phenyl-6-azapentalene)(2-methyl-4-(4'-s-butylphenyl)indenyl)zirconium dichloride
dimethylsilanediyl(2-methyl-4-thiapentalene)(2-methyl-4-(4'-sec-butylphenyl)indenyl)zirconium dichloride
dimethylsilanediyl(2-methyl-5-thiapentalene)(2-methyl-4-(4'-sec-butylphenyl)indenyl)zirconium dichloride
dimethylsilanediyl(2-methyl-6-thiapentalene)(2-methyl-4-(4'-sec-butylphenyl)indenyl)zirconium dichloride
dimethylsilanediyl(2,5-dimethyl-4-thiapentalene)(2-methyl-4-(4'-sec-butylphenyl)indenyl)zirconium dichloride
dimethylsilanediyl(2,5-dimethyl-6-thiapentalene)(2-methyl-4-(4'-sec-butylphenyl)indenyl)zirconium dichloride
dimethylsilanediyl(2-methyl-4-oxapentalene)(2-methyl-4-(4'-sec-butylphenyl)indenyl)zirconium dichloride
dimethylsilanediyl(2-methyl-5-oxapentalene)(2-methyl-4-(4'-sec-butylphenyl)indenyl)zirconium dichloride
dimethylsilanediyl(2-methyl-6-oxapentalene)(2-methyl-4-(4'-sec-butylphenyl)indenyl)zirconium dichloride
dimethylsilanediyl(2,5-dimethyl-4-oxapentalene)(2-methyl-4-(4'-sec-butylphenyl)indenyl)zirconium dichloride
dimethylsilanediyl(2,5-dimethyl-6-oxapentalene)(2-methyl-4-(4'-sec-butylphenyl)indenyl)zirconium dichloride
dimethylsilanediyl(2-methyl-4-azapentalene)(2-methyl-4-(4'-tert-butylphenyl)indenyl)zirconium dichloride
dimethylsilanediyl(2-methyl-5-azapentalene)(2-methyl-4-(4'-tert-butylphenyl)indenyl)zirconium dichloride
dimethylsilanediyl(2-methyl-6-azapentalene)(2-methyl-4-(4'-tert-butylphenyl)indenyl)zirconium dichloride
dimethylsilanediyl(2-methyl-N-phenyl-4-azapentalene)(2-methyl-4-(4'-tert-butylphenyl)indenyl)zirconium dichloride
dimethylsilanediyl(2-methyl-N-phenyl-5-azapentalene)(2-methyl-4-(4'-tert-butylphenyl)indenyl)zirconium dichloride
dimethylsilanediyl(2-methyl-N-phenyl-6-azapentalene)(2-methyl-4-(4'-tert-butylphenyl)indenyl)zirconium dichloride
dimethylsilanediyl(2,5-dimethyl-4-azapentalene)(2-methyl-4-(4'-tert-butylphenyl)indenyl)zirconium dichloride
dimethylsilanediyl(2,5-dimethyl-6-azapentalene)(2-methyl-4-(4'-tert-butylphenyl)indenyl)zirconium dichloride
dimethylsilanediyl(2,5-dimethyl-N-phenyl-4-azapentalene)(2-methyl-4-(4'-tert-butylphenyl)indenyl)zirconium dichloride
dimethylsilanediyl(2,5-dimethyl-N-phenyl-6-azapentalene)(2-methyl-4-(4'-tert-butylphenyl)indenyl)zirconium dichloride
dimethylsilanediyl(2-methyl-4-thiapentalene)(2-methyl-4-(4'-tert-butylphenyl)indenyl)zirconium dichloride
dimethylsilanediyl(2-methyl-5-thiapentalene)(2-methyl-4-(4'-tert-butylphenyl)indenyl)zirconium dichloride
dimethylsilanediyl(2-methyl-6-thiapentalene)(2-methyl-4-(4'-tert-butylphenyl)indenyl)zirconium dichloride
dimethylsilanediyl(2,5-dimethyl-4-thiapentalene)(2-methyl-4-(4'-tert-butylphenyl)indenyl)zirconium dichloride
dimethylsilanediyl(2,5-dimethyl-6-thiapentalene)(2-methyl-4-(4'-tert-butylphenyl)indenyl)zirconium dichloride
dimethylsilanediyl(2-methyl-4-oxapentalene)(2-methyl-4-(4'-tert-butylphenyl)indenyl)zirconium dichloride
dimethylsilanediyl(2-methyl-5-oxapentalene)(2-methyl-4-(4'-tert-butylphenyl)indenyl)zirconium dichloride
dimethylsilanediyl(2-methyl-6-oxapentalene)(2-methyl-4-(4'-tert-butylphenyl)indenyl)zirconium dichloride
dimethylsilanediyl(2,5-dimethyl-4-oxapentalene)(2-methyl-4-(4'-tert-butylphenyl)indenyl)zirconium dichloride
dimethylsilanediyl(2,5-dimethyl-6-oxapentalene)(2-methyl-4-(4'-tert-butylphenyl)indenyl)zirconium dichloride
dimethylsilanediyl(2-methyl-4-azapentalene)(2-methyl-4-(4'-n-pentylphenyl)indenyl)zirconium dichloride
dimethylsilanediyl(2-methyl-5-azapentalene)(2-methyl-4-(4'-n-pentylphenyl)indenyl)zirconium dichloride
dimethylsilanediyl(2-methyl-6-azapentalene)(2-methyl-4-(4'-n-pentylphenyl)indenyl)zirconium dichloride
dimethylsilanediyl(2-methyl-N-phenyl-4-azapentalene)(2-methyl-4-(4'-n-pentylphenyl)indenyl)zirconium dichloride
dimethylsilanediyl(2-methyl-N-phenyl-5-azapentalene)(2-methyl-4-(4'-n-pentylphenyl)indenyl)zirconium dichloride
dimethylsilanediyl(2-methyl-N-phenyl-6-azapentalene)(2-methyl-4-(4'-n-pentylphenyl)indenyl)zirconium dichloride
dimethylsilanediyl(2,5-dimethyl-4-azapentalene)(2-methyl-4-(4'-n-pentylphenyl)indenyl)zirconium dichloride
dimethylsilanediyl(2,5-dimethyl-6-azapentalene)(2-methyl-4-(4'-n-pentylphenyl)indenyl)zirconium dichloride
dimethylsilanediyl(2,5-dimethyl-N-phenyl-4-azapentalene)(2-methyl-4-(4'-n-pentylphenyl)indenyl)zirconium dichloride
dimethylsilanediyl(2,5-dimethyl-N-phenyl-6-azapentalene)(2-methyl-4-(4'-n-pentylphenyl)indenyl)zirconium dichloride
dimethylsilanediyl(2-methyl-4-thiapentalene)(2-methyl-4-(4'-n-pentylphenyl)indenyl)zirconium dichloride dimethylsilanediyl(2-methyl-5-thiapentalene)(2-methyl-4-(4'-n-pentylphenyl)indenyl)zirconium dichloride
dimethylsilanediyl(2-methyl-6-thiapentalene)(2-methyl-4-(4'-n-pentylphenyl)indenyl)zirconium dichloride
dimethylsilanediyl(2,5-dimethyl-4-thiapentalene)(2-methyl-4-(4'-n-pentylphenyl)indenyl)zirconium dichloride
dimethylsilanediyl(2,5-dimethyl-6-thiapentalene)(2-methyl-4-(4'-n-pentylphenyl)indenyl)zirconium dichloride
dimethylsilanediyl(2-methyl-4-oxapentalene)(2-methyl-4-(4'-n-pentylphenyl)indenyl)zirconium dichloride
dimethylsilanediyl(2-methyl-5-oxapentalene)(2-methyl-4-(4'-n-pentylphenyl)indenyl)zirconium dichloride
dimethylsilanediyl(2-methyl-6-oxapentalene)(2-methyl-4-(4'-n-pentylphenyl)indenyl)zirconium dichloride
dimethylsilanediyl(2,5-dimethyl-4-oxapentalene)(2-methyl-4-(4'-n-pentylphenyl)indenyl)zirconium dichloride
dimethylsilanediyl(2,5-dimethyl-6-oxapentalene)(2-methyl-4-(4'-n-pentylphenyl)indenyl)zirconium dichloride
dimethylsilanediyl(2-methyl-4-azapentalene)(2-methyl-4-(4'-n-hexylphenyl)indenyl)zirconium dichloride
dimethylsilanediyl(2-methyl-5-azapentalene)(2-methyl-4-(4'-n-hexylphenyl)indenyl)zirconium dichloride
dimethylsilanediyl(2-methyl-6-azapentalene)(2-methyl-4-(4'-n-hexylphenyl)indenyl)zirconium dichloride
dimethylsilanediyl(2-methyl-N-phenyl-4-azapentalene)(2-methyl-4-(4'-n-hexylphenyl)indenyl)zirconium dichloride
dimethylsilanediyl(2-methyl-N-phenyl-5-azapentalene)(2-methyl-4-(4'-n-hexylphenyl)indenyl)zirconium dichloride
dimethylsilanediyl(2-methyl-N-phenyl-6-azapentalene)(2-methyl-4-(4'-n-hexylphenyl)indenyl)zirconium dichloride
dimethylsilanediyl(2,5-dimethyl-4-azapentalene)(2-methyl-4-(4'-n-hexylphenyl)indenyl)zirconium dichloride
dimethylsilanediyl(2,5-dimethyl-6-azapentalene)(2-methyl-4-(4'-n-hexylphenyl)indenyl)zirconium dichloride
dimethylsilanediyl(2,5-dimethyl-N-phenyl-4-azapentalene)(2-methyl-4-(4'-n-hexylphenyl)indenyl)zirconium dichloride
dimethylsilanediyl(2,5-dimethyl-N-phenyl-6-azapentalene)(2-methyl-4-(4'-n-hexylphenyl)indenyl)zirconium dichloride
dimethylsilanediyl(2-methyl-4-thiapentalene)(2-methyl-4-(4'-n-hexylphenyl)indenyl)zirconium dichloride
dimethylsilanediyl(2-methyl-5-thiapentalene)(2-methyl-4-(4'-n-hexylphenyl)indenyl)zirconium dichloride
dimethylsilanediyl(2-methyl-6-thiapentalene)(2-methyl-4-(4'-n-hexylphenyl)indenyl)zirconium dichloride
dimethylsilanediyl(2,5-dimethyl-4-thiapentalene)(2-methyl-4-(4'-n-hexylphenyl)indenyl)zirconium dichloride
dimethylsilanediyl(2,5-dimethyl-6-thiapentalene)(2-methyl-4-(4'-n-hexylphenyl)indenyl)zirconium dichloride
dimethylsilanediyl(2-methyl-4-oxapentalene)(2-methyl-4-(4'-n-hexylphenyl)indenyl)zirconium dichloride
dimethylsilanediyl(2-methyl-5-oxapentalene)(2-methyl-4-(4'-n-hexylphenyl)indenyl)zirconium dichloride
dimethylsilanediyl(2-methyl-6-oxapentalene)(2-methyl-4-(4'-n-hexylphenyl)indenyl)zirconium dichloride
dimethylsilanediyl(2,5-dimethyl-4-oxapentalene)(2-methyl-4-(4'-n-hexylphenyl)indenyl)zirconium dichloride
dimethylsilanediyl(2,5-dimethyl-6-oxapentalene)(2-methyl-4-(4'-n-hexylphenyl)indenyl)zirconium dichloride
dimethylsilanediyl(2-methyl-4-azapentalene)(2-methyl-4-(4'-cyclohexylphenyl)indenyl)zirconium dichloride
dimethylsilanediyl(2-methyl-5-azapentalene)(2-methyl-4-(4'-cyclohexylphenyl)indenyl)zirconium dichloride
dimethylsilanediyl(2-methyl-6-azapentalene)(2-methyl-4-(4'-cyclohexylphenyl)indenyl)zirconium dichloride
dimethylsilanediyl(2-methyl-N-phenyl-4-azapentalene)(2-methyl-4-(4'-cyclohexylphenyl)indenyl)zirconium dichloride
dimethylsilanediyl(2-methyl-N-phenyl-5-azapentalene)(2-methyl-4-(4'-cyclohexylphenyl)indenyl)zirconium dichloride
dimethylsilanediyl(2-methyl-N-phenyl-6-azapentalene)(2-methyl-4-(4'-cyclohexylphenyl)indenyl)zirconium dichloride
dimethylsilanediyl(2,5-dimethyl-4-azapentalene)(2-methyl-4-(4'-cyclohexylphenyl)indenyl)zirconium dichloride
dimethylsilanediyl(2,5-dimethyl-6-azapentalene)(2-methyl-4-(4'-cyclohexylphenyl)indenyl)zirconium dichloride
dimethylsilanediyl(2,5-dimethyl-N-phenyl-4-azapentalene)(2-methyl-4-(4'-cyclohexylphenyl)indenyl)zirconium dichloride
dimethylsilanediyl(2,5-dimethyl-N-phenyl-6-azapentalene)(2-methyl-4-(4'-cyclohexylphenyl)indenyl)zirconium dichloride
dimethylsilanediyl(2-methyl-4-thiapentalene)(2-methyl-4-(4'-cyclohexylphenyl)indenyl)zirconium dichloride
dimethylsilanediyl(2-methyl-5-thiapentalene)(2-methyl-4-(4'-cyclohexylphenyl)indenyl)zirconium dichloride
dimethylsilanediyl(2-methyl-6-thiapentalene)(2-methyl-4-(4'-cyclohexylphenyl)indenyl)zirconium dichloride
dimethylsilanediyl(2,5-dimethyl-4-thiapentalene)(2-methyl-4-(4'-cyclohexylphenyl)indenyl)zirconium dichloride
dimethylsilanediyl(2,5-dimethyl-6-thiapentalene)(2-methyl-4-(4'-cyclohexylphenyl)indenyl)zirconium dichloride
dimethylsilanediyl(2-methyl-4-oxapentalene)(2-methyl-4-(4'-cyclohexylphenyl)indenyl)zirconium dichloride
dimethylsilanediyl(2-methyl-5-oxapentalene)(2-methyl-4-(4'-cyclohexylphenyl)indenyl)zirconium dichloride
dimethylsilanediyl(2-methyl-6-oxapentalene)(2-methyl-4-(4'-cyclohexylphenyl)indenyl)zirconium dichloride
dimethylsilanediyl(2,5-dimethyl-4-oxapentalene)(2-methyl-4-(4'-cyclohexylphenyl)indenyl)zirconium dichloride
dimethylsilanediyl(2,5-dimethyl-6-oxapentalene)(2-methyl-4-(4'-cyclohexylphenyl)indenyl)zirconium dichloride
dimethylsilanediyl(2-methyl-4-azapentalene)(2-methyl-4-(4'-trimethylsilylphenyl)indenyl)zirconium dichloride
dimethylsilanediyl(2-methyl-5-azapentalene)(2-methyl-4-(4'-trimethylsilylphenyl)indenyl)zirconium dichloride
dimethylsilanediyl(2-methyl-6-azapentalene)(2-methyl-4-(4'-trimethylsilylphenyl)indenyl)zirconium dichloride
dimethylsilanediyl(2-methyl-N-phenyl-4-azapentalene)(2-methyl-4-(4'-trimethylsilylphenyl)indenyl)zirconium dichloride
dimethylsilanediyl(2-methyl-N-phenyl-5-azapentalene)(2-methyl-4-(4'-trimethylsilylphenyl)indenyl)zirconium dichloride
dimethylsilanediyl(2-methyl-N-phenyl-6-azapentalene)(2-methyl-4-(4'-trimethylsilylphenyl)indenyl)zirconium dichloride
dimethylsilanediyl(2,5-dimethyl-4-azapentalene)(2-methyl-4-(4'-trimethylsilylphenyl)indenyl)zirconium dichloride
dimethylsilanediyl(2,5-dimethyl-6-azapentalene)(2-methyl-4-(4'-trimethylsilylphenyl)indenyl)zirconium dichloride
dimethylsilanediyl(2,5-dimethyl-N-phenyl-4-azapentalene)(2-methyl-4-(4'-trimethylsilylphenyl)indenyl)zirconium dichloride dimethylsilanediyl(2,5-dimethyl-N-phenyl-6-azapentalene)(2-methyl-4-(4'-trimethylsilylphenyl)indenyl)zirconium dichloride
dimethylsilanediyl(2-methyl-4-thiapentalene)(2-methyl-4-(4'-trimethylsilylphenyl)indenyl)zirconium dichloride
dimethylsilanediyl(2-methyl-5-thiapentalene)(2-methyl-4-(4'-trimethylsilylphenyl)indenyl)zirconium dichloride
dimethylsilanediyl(2-methyl-6-thiapentalene)(2-methyl-4-(4'-trimethylsilylphenyl)indenyl)zirconium dichloride
dimethylsilanediyl(2,5-dimethyl-4-thiapentalene)(2-methyl-4-(4'-trimethylsilylphenyl)indenyl)zirconium dichloride
dimethylsilanediyl(2,5-dimethyl-6-thiapentalene)(2-methyl-4-(4'-trimethylsilylphenyl)indenyl)zirconium dichloride
dimethylsilanediyl(2-methyl-4-oxapentalene)(2-methyl-4-(4'-trimethylsilylphenyl)indenyl)zirconium dichloride
dimethylsilanediyl(2-methyl-5-oxapentalene)(2-methyl-4-(4'-trimethylsilylphenyl)indenyl)zirconium dichloride
dimethylsilanediyl(2-methyl-6-oxapentalene)(2-methyl-4-(4'-trimethylsilylphenyl)indenyl)zirconium dichloride
dimethylsilanediyl(2,5-dimethyl-4-oxapentalene)(2-methyl-4-(4'-trimethylsilylphenyl)indenyl)zirconium dichloride
dimethylsilanediyl(2,5-dimethyl-6-oxapentalene)(2-methyl-4-(4'-trimethylsilylphenyl)indenyl)zirconium dichloride
dimethylsilanediyl(2-methyl-4-azapentalene)(2-methyl-4-(4'-adamantylphenyl)indenyl)zirconium dichloride
dimethylsilanediyl(2-methyl-5-azapentalene)(2-methyl-4-(4'-adamantylphenyl)indenyl)zirconium dichloride
dimethylsilanediyl(2-methyl-6-azapentalene)(2-methyl-4-(4'-adamantylphenyl)indenyl)zirconium dichloride
dimethylsilanediyl(2-methyl-N-phenyl-4-azapentalene)(2-methyl-4-(4'-adamantylphenyl)indenyl)zirconium dichloride
dimethylsilanediyl(2-methyl-N-phenyl-5-azapentalene)(2-methyl-4-(4'-adamantylphenyl)indenyl)zirconium dichloride
dimethylsilanediyl(2-methyl-N-phenyl-6-azapentalene)(2-methyl-4-(4'-adamantylphenyl)indenyl)zirconium dichloride
dimethylsilanediyl(2,5-dimethyl-4-azapentalene)(2-methyl-4-(4'-adamantylphenyl)indenyl)zirconium dichloride
dimethylsilanediyl(2,5-dimethyl-6-azapentalene)(2-methyl-4-(4'-adamantylphenyl)indenyl)zirconium dichloride
dimethylsilanediyl(2,5-dimethyl-4-azapentalene)(2-methyl-4-(4'-adamantylphenyl)indenyl)zirconium dichloride
dimethylsilanediyl(2,5-dimethyl-N-phenyl-4-azapentalene)(2-methyl-4-(4'-adamantylphenyl)indenyl)zirconium dichloride
dimethylsilanediyl(2,5-dimethyl-N-phenyl-6-azapentalene)(2-methyl-4-(4'-adamantylphenyl)indenyl)zirconium dichloride
dimethylsilanediyl(2-methyl-4-thiapentalene)(2-methyl-4-(4'-adamantylphenyl)indenyl)zirconium dichloride
dimethylsilanediyl(2-methyl-5-thiapentalene)(2-methyl-4-(4'-adamantylphenyl)indenyl)zirconium dichloride
dimethylsilanediyl(2-methyl-6-thiapentalene)(2-methyl-4-(4'-adamantylphenyl)indenyl)zirconium dichloride
dimethylsilanediyl(2,5-dimethyl-4-thiapentalene)(2-methyl-4-(4'-adamantylphenyl)indenyl)zirconium dichloride
dimethylsilanediyl(2,5-dimethyl-6-thiapentalene)(2-methyl-4-(4'-adamantylphenyl)indenyl)zirconium dichloride
dimethylsilanediyl(2-methyl-4-oxapentalene)(2-methyl-4-(4'-adamantylphenyl)indenyl)zirconium dichloride
dimethylsilanediyl(2-methyl-5-oxapentalene)(2-methyl-4-(4'-adamantylphenyl)indenyl)zirconium dichloride
dimethylsilanediyl(2-methyl-6-oxapentalene)(2-methyl-4-(4'-adamantylphenyl)indenyl)zirconium dichloride
dimethylsilanediyl(2,5-dimethyl-4-oxapentalene)(2-methyl-4-(4'-adamantylphenyl)indenyl)zirconium dichloride
dimethylsilanediyl(2,5-dimethyl-6-oxapentalene)(2-methyl-4-(4'-adamantylphenyl)indenyl)zirconium dichloride
dimethylsilanediyl(2-methyl-4-azapentalene)(2-methyl-4-(4'-tris-(trifluoromethyl)methylphenyl)indenyl)zirconium dichloride
dimethylsilanediyl(2-methyl-5-azapentalene)(2-methyl-4-(4'-tris-(trifluoromethyl)methylphenyl)indenyl)zirconium dichloride
dimethylsilanediyl(2-methyl-6-azapentalene)(2-methyl-4-(4'-tris-(trifluoromethyl)methylphenyl)indenyl)zirconium dichloride
dimethylsilanediyl(2-methyl-N-phenyl-4-azapentalene)(2-methyl-4-(4'-tris(trifluoromethyl)methylphenyl)indenyl)zirconium dichloride
dimethylsilanediyl(2-methyl-N-phenyl-5-azapentalene)(2-methyl-4-(4'-tris(trifluoromethyl)methylphenyl)indenyl)zirconium dichloride
dimethylsilanediyl(2-methyl-N-phenyl-6-azapentalene)(2-methyl-4-(4'-tris(trifluoromethyl)methylphenyl)indenyl)zirconium dichloride
dimethylsilanediyl(2,5-dimethyl-4-azapentalene)(2-methyl-4-(4'-tris(trifluoromethyl)methylphenyl)indenyl)zirconium dichloride
dimethylsilanediyl(2,5-dimethyl-6-azapentalene)(2-methyl-4-(4'-tris(trifluoromethyl)methylphenyl)indenyl)zirconium dichloride
dimethylsilanediyl(2,5-dimethyl-N-phenyl-4-azapentalene)(2-methyl-4-(4'-tris(trifluoromethyl)methylphenyl)indenyl)zirconium dichloride
dimethylsilanediyl(2,5-dimethyl-N-phenyl-6-azapentalene)(2-methyl-4-(4'-tris(trifluoromethyl)methylphenyl)indenyl)zirconium dichloride
dimethylsilanediyl(2-methyl-4-thiapentalene)(2-methyl-4-(4'-tris-(trifluoromethyl)methylphenyl)indenyl)zirconium dichloride
dimethylsilanediyl(2-methyl-5-thiapentalene)(2-methyl-4-(4'-tris-(trifluoromethyl)methylphenyl)indenyl)zirconium dichloride
dimethylsilanediyl(2-methyl-6-thiapentalene)(2-methyl-4-(4'-tris-(trifluoromethyl)methylphenyl)indenyl)zirconium dichloride
dimethylsilanediyl(2,5-dimethyl-4-thiapentalene)(2-methyl-4-(4'-tris(trifluoromethyl)methylphenyl)indenyl)zirconium dichloride
dimethylsilanediyl(2,5-dimethyl-6-thiapentalene)(2-methyl-4-(4'-tris(trifluoromethyl)methylphenyl)indenyl)zirconium dichloride
dimethylsilanediyl(2-methyl-4-oxapentalene)(2-methyl-4-(4'-tris-(trifluoromethyl)methylphenyl)indenyl)zirconium dichloride
dimethylsilanediyl(2-methyl-5-oxapentalene)(2-methyl-4-(4'-tris-(trifluoromethyl)methylphenyl)indenyl)zirconium dichloride
dimethylsilanediyl(2-methyl-6-oxapentalene)(2-methyl-4-(4'-tris-(trifluoromethyl)methylphenyl)indenyl)zirconium dichloride
dimethylsilanediyl(2,5-dimethyl-4-oxapentalene)(2-methyl-4-(4'-tris(trifluoromethyl)methylphenyl)indenyl)zirconium dichloride
dimethylsilanediyl(2,5-dimethyl-6-oxapentalene)(2-methyl-4-(4'-tris(trifluoromethyl)methylphenyl)indenyl)zirconium dichloride dimethylsilanediyl(2-methyl-4-azapentalene)(2-ethyl-4-(4'-tert-butylphenyl)indenyl)zirconium dichloride
dimethylsilanediyl(2-methyl-5,6-dihydro-4-azapentalene)(2-ethyl-4'-(4'-tert-butylphenyl)indenyl)zirconium dichloride
dimethylsilanediyl(2-methyl-4-azapentalene)(2-ethyl-4-(4'-tert-butylphenyl-tetrahydroindenyl)zirconium dichloride
dimethylsilanediyl(2-methyl-5-azapentalene)(2-n-butyl-4-(4'-tert-butylphenyl)indenyl)zirconium dichloride
ethylidene(2-methyl-6-azapentalene)(2-methyl-4-(4'-tert-butyl-phenyl)indenyl)zirconium dichloride
dimethylsilanediyl(2-methyl-N-trimethylsilyl-4-azapentalene)(2-methyl-4-(4'-tert-butylphenyl)indenyl)zirconium dichloride
dimethylsilanediyl(2-methyl-N-tolyl-5-azapentalene)(2-n-propyl-4-(4'-tert-butylphenyl)indenyl)zirconium dichloride
dimethylgermanediyl(2-methyl-N-phenyl-6-azapentalene)(2-methyl-4-(4'-tert-butylphenyl)indenyl)zirconium dichloride
methylethylidene(2,5-dimethyl-4-azapentalene)(2-methyl-4-(4'-tert-butylphenyl)indenyl)zirconium dichloride
dimethylsilanediyl(2,5-diisopropyl-6-azapentalene)(2-methyl-4-(4'-tert-butylphenyl)indenyl)zirconium dichloride
dimethylsilanediyl(2,5-dimethyl-N-phenyl-4-azapentalene)(2,6-dimethyl-4-(4'-tert-butylphenyl)indenyl)zirconium dichloride
dimethylsilanediyl(2,5-dimethyl-N-phenyl-6-azapentalene)(2-methyl-4-(6'-tert-butylnaphthylindenyl)zirconium dichloride
dimethylsilanediyl(2,5-dimethyl-N-phenyl-6-azapentalene)(2-methyl-4-(6'-tert-butylanthracenylindenyl)zirconium dichloride
dimethylsilanediyl(2-methyl-4-phosphapentalene)(2-methyl-4-(4'-tert-butylphenyl)indenyl)zirconium dichloride
diphenylsilanediyl(2-methyl-5-thiapentalene)(2-methyl-4-(4'-tert-butylphenyl)indenyl)zirconium dichloride
methylphenylsilanediyl(2-methyl-6-thiapentalene)(2-methyl-4-(4'-tert-butylphenyl)indenyl)zirconium dichloride
methylidene(2,5-dimethyl-4-thiapentalene)(2-methyl-4-(4'-tert-butylphenyl)indenyl)zirconium dichloride
dimethylmethylidene(2,5-dimethyl-6-thiapentalene)(2-methyl-4-(4'-tert-butylphenyl)indenyl)zirconium dichloride
diphenylsilanediyl(2,5-dimethyl-4-oxapentalene)(2-methyl-4-(4'-tert-butylphenyl)indenyl)zirconium dichloride
diphenylsilanediyl(2,5-dimethyl-6-oxapentalene)(2-methyl-4-(4'-tert-butylphenyl)indenyl)zirconium dichloride
dimethylsilanediyl(2-methyl-4-azapentalene)(2-methylindenyl)-zirconium dichloride
dimethylsilanediyl(2-methyl-5-azapentalene)(2-methylindenyl)-zirconium dichloride
dimethylsilanediyl(2-methyl-6-azapentalene)(2-methylindenyl)-zirconium dichloride
dimethylsilanediyl(2-methyl-N-phenyl-4-azapentalene)(2-methyl-indenyl)zirconium dichloride
dimethylsilanediyl(2-methyl-N-phenyl-5-azapentalene)(2-methyl-indenyl)zirconium dichloride
dimethylsilanediyl(2-methyl-N-phenyl-6-azapentalene)(2-methyl-indenyl)zirconium dichloride
dimethylsilanediyl(2,5-dimethyl-4-azapentalene)(2-methyl-indenyl)-zirconium dichloride
dimethylsilanediyl(2,5-dimethyl-6-azapentalene)(2-methyl-indenyl)-zirconium dichloride
dimethylsilanediyl(2,5-dimethyl-N-phenyl-4-azapentalene)(2-methylindenyl)zirconium dichloride
dimethylsilanediyl(2,5-dimethyl-N-phenyl-6-azapentalene)(2-methylindenyl)zirconium dichloride
dimethylsilanediyl(2-methyl-4-thiapentalene)(2-methylindenyl)-zirconium dichloride
dimethylsilanediyl(2-methyl-5-thiapentalene)(2-methylindenyl)-zirconium dichloride
dimethylsilanediyl(2-methyl-6-thiapentalene)(2-methylindenyl)-zirconium dichloride
dimethylsilanediyl(2,5-dimethyl-4-thiapentalene)(2-methyl-indenyl)zirconium dichloride
dimethylsilanediyl(2,5-dimethyl-6-thiapentalene)(2-methyl-indenyl)zirconium dichloride
dimethylsilanediyl(2-methyl-4-oxapentalene)(2-methylindenyl)-zirconium dichloride
dimethylsilanediyl(2-methyl-5-oxapentalene)(2-methylindenyl)-zirconium dichloride
dimethylsilanediyl(2-methyl-6-oxapentalene)(2-methylindenyl)-zirconium dichloride
dimethylsilanediyl(2,5-dimethyl-4-oxapentalene)(2-methyl-indenyl)-zirconium dichloride
dimethylsilanediyl(2,5-dimethyl-6-oxapentalene)(2-methyl-indenyl)-zirconium dichloride
dimethylsilanediyl(2-methyl-4-azapentalene)(indenyl)zirconium dichloride
dimethylsilanediyl(2-methyl-5-azapentalene)(indenyl)zirconium dichloride
dimethylsilanediyl(2-methyl-6-azapentalene)(indenyl)zirconium dichloride
dimethylsilanediyl(2-methyl-N-phenyl-4-azapentalene)(indenyl)-zirconium dichloride
dimethylsilanediyl(2-methyl-N-phenyl-5-azapentalene)(indenyl)-zirconium dichloride
dimethylsilanediyl(2-methyl-N-phenyl-6-azapentalene)(indenyl)-zirconium dichloride
dimethylsilanediyl(2,5-dimethyl-4-azapentalene)(indenyl)zirconium dichloride
dimethylsilanediyl(2,5-dimethyl-6-azapentalene)(indenyl)zirconium dichloride
dimethylsilanediyl(2,5-dimethyl-N-phenyl-4-azapentalene)-(indenyl)zirconium dichloride
dimethylsilanediyl(2,5-dimethyl-N-phenyl-6-azapentalene)(indenyl) zirconium dichloride
dimethylsilanediyl(2-methyl-4-thiapentalene)(indenyl)zirconium dichloride
dimethylsilanediyl(2-methyl-5-thiapentalene)(indenyl)zirconium dichloride
dimethylsilanediyl(2-methyl-6-thiapentalene)(indenyl)zirconium dichloride
dimethylsilanediyl(2,5-dimethyl-4-thiapentalene)(indenyl)-zirconium dichloride
dimethylsilanediyl(2,5-dimethyl-6-thiapentalene)(indenyl)-zirconium dichloride
dimethylsilanediyl(2-methyl-4-oxapentalene)(indenyl)zirconium dichloride
dimethylsilanediyl(2-methyl-5-oxapentalene)(indenyl)zirconium dichloride
dimethylsilanediyl(2-methyl-6-oxapentalene)(indenyl)zirconium dichloride
dimethylsilanediyl(2,5-dimethyl-4-oxapentalene)(indenyl) zirconium dichloride
dimethylsilanediyl(2,5-dimethyl-6-oxapentalene)(indenyl) zirconium dichloride
dimethylsilanediyl(2-methyl-4-azapentalene)(2-methyl-4-phenyl-indenyl)zirconium dichloride
dimethylsilanediyl(2-methyl-5-azapentalene)(2-methyl-4-phenyl-indenyl)zirconium dichloride
dimethylsilanediyl(2-methyl-6-azapentalene)(2-methyl-4-phenyl-indenyl)zirconium dichloride dimethylsilanediyl(2-methyl-N-phenyl-4-azapentalene)(2-methyl-4-phenylindenyl)zirconium dichloride
dimethylsilanediyl(2-methyl-N-phenyl-5-azapentalene)(2-methyl-4-phenylindenyl)zirconium dichloride
dimethylsilanediyl(2-methyl-N-phenyl-6-azapentalene)(2-methyl-4-phenylindenyl)zirconium dichloride
dimethylsilanediyl(2,5-dimethyl-4-azapentalene)(2-methyl-4-phenyl indenyl)zirconium dichloride
dimethylsilanediyl(2,5-dimethyl-6-azapentalene)(2-methyl-4-phenyl indenyl)zirconium dichloride
dimethylsilanediyl(2,5-dimethyl-N-phenyl-4-azapentalene)(2-methyl-4-phenylindenyl)zirconium dichloride
dimethylsilanediyl(2,5-dimethyl-N-phenyl-6-azapentalene)(2-methyl-4-phenylindenyl)zirconium dichloride
dimethylsilanediyl(2-methyl-4-thiapentalene)(2-methyl-4-phenyl-indenyl)zirconium dichloride
dimethylsilanediyl(2-methyl-5-thiapentalene)(2-methyl-4-phenyl-indenyl)zirconium dichloride
dimethylsilanediyl(2-methyl-6-thiapentalene)(2-methyl-4-phenyl-indenyl)zirconium dichloride
dimethylsilanediyl(2,5-dimethyl-4-thiapentalene)(2-methyl-4-phenylindenyl)zirconium dichloride
dimethylsilanediyl(2,5-dimethyl-6-thiapentalene)(2-methyl-4-phenylindenyl)zirconium dichloride
dimethylsilanediyl(2-methyl-4-oxapentalene)(2-methyl-4-phenyl-indenyl)zirconium dichloride
dimethylsilanediyl(2-methyl-5-oxapentalene)(2-methyl-4-phenyl-indenyl)zirconium dichloride
dimethylsilanediyl(2-methyl-6-oxapentalene)(2-methyl-4-phenyl-indenyl)zirconium dichloride
dimethylsilanediyl(2,5-dimethyl-4-oxapentalene)(2-methyl-4-phenylindenyl)zirconium dichloride
dimethylsilanediyl(2,5-dimethyl-6-oxapentalene)(2-methyl-4-phenylindenyl)zirconium dichloride
dimethylsilanediyl(2-methyl-4-azapentalene)(2-methyl-4,5-benzo-indenyl)zirconium dichloride
dimethylsilanediyl(2-methyl-5-azapentalene)(2-methyl-4,5-benzo-indenyl)zirconium dichloride
dimethylsilanediyl(2-methyl-6-azapentalene)(2-methyl-4,5-benzo-indenyl)zirconium dichloride
dimethylsilanediyl(2-methyl-N-phenyl-4-azapentalene)(2-methyl-4,5-benzoindenyl)zirconium dichloride
dimethylsilanediyl(2-methyl-N-phenyl-5-azapentalene)(2-methyl-4,5-benzoindenyl)zirconium dichloride
dimethylsilanediyl(2-methyl-N-phenyl-6-azapentalene)(2-methyl-4,5-benzoindenyl)zirconium dichloride
dimethylsilanediyl(2,5-dimethyl-4-azapentalene)(2-methyl-4,5-benzoindenyl)zirconium dichloride
dimethylsilanediyl(2,5-dimethyl-6-azapentalene)(2-methyl-4,5-benzoindenyl)zirconium dichloride
dimethylsilanediyl(2,5-dimethyl-N-phenyl-4-azapentalene)(2-methyl-4,5-benzoindenyl)zirconium dichloride
dimethylsilanediyl(2,5-dimethyl-N-phenyl-6-azapentalene)(2-methyl-4,5-benzoindenyl)zirconium dichloride
dimethylsilanediyl(2-methyl-4-thiapentalene)(2-methyl-4,5-benzo-indenyl)zirconium dichloride
dimethylsilanediyl(2-methyl-5-thiapentalene)(2-methyl-4,5-benzo-indenyl)zirconium dichloride
dimethylsilanediyl(2-methyl-6-thiapentalene)(2-methyl-4,5-benzo-indenyl)zirconium dichloride
dimethylsilanediyl(2,5-dimethyl-4-thiapentalene)(2-methyl-4,5-benzoindenyl)zirconium dichloride
dimethylsilanediyl(2,5-dimethyl-6-thiapentalene)(2-methyl-4,5-benzoindenyl)zirconium dichloride
dimethylsilanediyl(2-methyl-4-oxapentalene)(2-methyl-4,5-benzo-indenyl)zirconium dichloride
dimethylsilanediyl(2-methyl-5-oxapentalene)(2-methyl-4,5-benzo-indenyl)zirconium dichloride
dimethylsilanediyl(2-methyl-6-oxapentalene)(2-methyl-4,5-benzo-indenyl)zirconium dichloride
dimethylsilanediyl(2,5-dimethyl-4-oxapentalene)(2-methyl-4,5-benzoindenyl)zirconium dichloride
dimethylsilanediyl(2,5-dimethyl-6-oxapentalene)(2-methyl-4,5-benzoindenyl)zirconium dichloride
dimethylsilanediylbis(2-methyl-4-azapentalene)zirconium dichloride
dimethylsilanediylbis(2-methyl-5-azapentalene)zirconium dichloride
dimethylsilanediylbis(2-methyl-6-azapentalene)zirconium dichloride
dimethylsilanediylbis(2-methyl-N-phenyl-4-azapentalene)zirconium dichloride
dimethylsilanediylbis(2-methyl-N-phenyl-5-azapentalene)zirconium dichloride
dimethylsilanediylbis(2-methyl-N-phenyl-6-azapentalene)zirconium dichloride
dimethylsilanediylbis(2,5-dimethyl-4-azapentalene)zirconium dichloride
dimethylsilanediylbis(2,5-dimethyl-6-azapentalene)zirconium dichloride
dimethylsilanediylbis(2,5-dimethyl-N-phenyl-4-azapentalene)-zirconium dichloride
dimethylsilanediylbis(2,5-dimethyl-N-phenyl-6-azapentalene)-zirconium dichloride
dimethylsilanediylbis(2-methyl-4-thiapentalene)zirconium dichloride
dimethylsilanediylbis(2-methyl-5-thiapentalene)zirconium dichloride
dimethylsilanediylbis(2-methyl-6-thiapentalene)zirconium dichloride
dimethylsilanediylbis(2,5-dimethyl-4-thiapentalene)zirconium dichloride
dimethylsilanediylbis(2,5-dimethyl-6-thiapentalene)zirconium dichloride
dimethylsilanediylbis(2-methyl-4-oxapentalene)zirconium dichloride
dimethylsilanediylbis(2-methyl-5-oxapentalene)zirconium dichloride
dimethylsilanediylbis(2-methyl-6-oxapentalene)zirconium dichloride
dimethylsilanediylbis(2,5-dimethyl-4-oxapentalene)zirconium dichloride
dimethylsilanediylbis(2,5-dimethyl-6-oxapentalene)zirconium dichloride.

Examples of further novel metallocenes are those of the above list in which the " . . . zirconium dichloride" is replaced by the groups
zirconium monochloride mono(2,4-di-tert-butylphenoxide)
zirconium monochloride mono(2,6-di-tert-butylphenoxide)
zirconium monochloride mono(3,5-di-tert-butylphenoxide)
zirconium monochloride mono(2,6-di-sec-butylphenoxide)
zirconium monochloride mono(2,4-dimethylphenoxide)
zirconium monochloride mono(2,3-dimethylphenoxide)
zirconium monochloride mono(2,5-dimethylphenoxide)
zirconium monochloride mono(2,6-dimethylphenoxide)
zirconium monochloride mono(3,4-dimethylphenoxide)
zirconium monochloride mono(3,5-dimethylphenoxide)
zirconium monochloromonophenoxide
zirconium monochloride mono(2-methylphenoxide)
zirconium monochloride mono(3-methylphenoxide)
zirconium monochloride mono(4-methylphenoxide)
zirconium monochloride mono(2-ethylphenoxide)
zirconium monochloride mono(3-ethylphenoxide)

zirconium monochloride mono(4-ethylphenoxide)
zirconium monochloride mono(2-sec-butylphenoxide)
zirconium monochloride mono(2-tert-butylphenoxide)
zirconium monochloride mono(3-tert-butylphenoxide)
zirconium monochloride mono(4-sec-butylphenoxide)
zirconium monochloride mono(4-tert-butylphenoxide)
zirconium monochloride mono(2-isopropyl-5-methylphenoxide)
zirconium monochloride mono(4-isopropyl-3-methylphenoxide)
zirconium monochloride mono(5-isopropyl-2-methylphenoxide)
zirconium monochloride mono(5-isopropyl-3-methylphenoxide)
zirconium monochloride mono(2,4-bis(2-methyl-2-butyl) phenoxide)
zirconium monochloride mono(2,6-di-tert-butyl-4-methylphenoxide)
zirconium monochloride mono(2,6-nonylphenoxide)
zirconium monochloride mono(4-naphthoxide)
zirconium monochloride mono(2-naphthoxide)
zirconium monochloride mono(2-phenylphenoxide)
zirconium monochloride mono(tert-butoxide)
zirconium monochloride mono(N-methylanilide)
zirconium monochloride mono(2-tert-butylanilide)
zirconium monochloride mono(tert-butylamide)
zirconium monochloride mono(di-isopropylamide)
zirconium monochloride monomethyl
zirconium monochloride monobenzyl
zirconium monochloride mononeopentyl.

Also preferred are the corresponding dimethylzirconium compounds, the corresponding zirconium-$\eta^4$-butadiene compounds and also the corresponding compounds having 1,2-(1-methylethanediyl), 1,2-(1,1-dimethylethanediyl) and 1,2-(1,2-dimethylethanediyl) bridges.

The catalyst system of the present invention comprises at least one Lewis base B) of the formula (IV), usually an organometallic transition metal compound which can be reacted in any desired stoichiometric ratio with compounds of the formula (I), (II) or (III).

(IV)

The radicals $R^{20}$ in formula (IV) may be identical or different and are each a halogen atom, a hydrogen atom, a $C_1$–$C_{40}$ group, preferably $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl or $C_7$–$C_{40}$-haloalkylaryl. $R^{20}$ are preferably $C_1$–$C_6$-alkyl groups, particularly preferably $C_1$–$C_4$-alkyl groups.

The catalyst system of the present invention is prepared using a molar ratio of boron from the compounds of the formulae (I) and/or (II) to $M^2$ from the compounds of the formula (III) of from 0.01 to 10,000. Preference is given to a molar ratio of from 0.1 to 1000, very particularly preferably from 1 to 100. In addition, a compound of the formula (IV) may be added in a molar ratio of Al:$M^2$ of from 0.01 to 10,000. Preference is given to a molar ratio of from 0.1 to 1000, very particularly preferably from 1 to 100.

The compounds may be brought into contact with one another in any conceivable combination. One possible procedure is to dissolve or suspend an organometallic transition metal compound of the formula (III) in an aliphatic or aromatic solvent such as toluene, heptane, tetrahydrofuran or diethyl ether. A compound of the formula (IV) in dissolved or suspended form is then added. The reaction time is from 1 minute to 24 hours, preferably from 5 minutes to 120 minutes. The reaction temperature is from −10° C. to +200° C., preferably from 0° C. to 50° C. Subsequently, an organoboron compound of the formula (I) or (II) either as such or in dissolved or in suspended form is added. The reaction time is from 1 minute to 24 hours, preferably from 5 minutes to 120 minutes. The reaction temperature is from −10° C. to +200° C., preferably from 0° C. to 50° C. The individual components can also be introduced into the polymerization vessel in succession, in any order.

If desired, the catalyst system of the present invention may also be supported. For this purpose, the catalyst system of the present invention can be reacted with a support component:

The catalyst system of the present invention further comprises at least one support component C) which may be any organic or inorganic, inert solid, in particular a porous support such as talc, inorganic oxides and finely divided polymer powders (e.g. polyolefins).

Suitable inorganic oxides are those of elements of groups 2, 3, 4, 5, 13, 14, 15 and 16 of the Periodic Table of the Elements. Examples of oxides preferred as supports include silicon dioxide, aluminum oxide and also mixed oxides and/or Mg/Al mixed oxide of the two elements and the corresponding oxide mixtures. Other inorganic oxides which can be used alone or in combination with the last-named preferred oxidic supports are, for example, MgO, $ZrO_2$, $TiO_2$ or $B_2O_3$, to name only a few.

The support materials used have a specific surface area in the range from 10 to 1000 m$^2$/g, a pore volume in the range from 0.1 to 5 ml/g and a mean particle size of from 1 to 500 μm. Preference is given to supports having a specific surface area in the range from 50 to 500 m$^2$/g, a pore volume in the range from 0.5 to 3.5 ml/g and a mean particle size in the range from 5 to 350 μm. Particular preference is given to supports having a specific surface area in the range from 200 to 400 m$^2$/g, a pore volume in the range from 0.8 to 3.0 ml/g and a mean particle size of from 10 to 200 μm.

If the support material used naturally has a low moisture content or residual solvent content, dehydration or drying before use can be omitted. If this is not the case, as when silica gel is used as support material, dehydration or drying is advisable. Thermal dehydration or drying of the support material can be carried out under reduced pressure with simultaneous inert gas blanketing (e.g. nitrogen). The drying temperature is in the range from 100 to 1000° C., preferably from 200 to 800° C. In this case, the pressure is not critical. The duration of the drying process can be from 1 to 24 hours. Shorter or longer drying times are possible, provided that equilibrium with the hydroxyl groups on the support surface can be established under the conditions selected, which normally requires from 4 to 8 hours.

Dehydration or drying of the support material can also be carried out by chemical means, by reacting the adsorbed water and the hydroxyl groups on the surface with suitable passivating agents. Reaction with the passivating reagent enables the hydroxyl groups to be converted completely or partially into a form which leads to no negative interaction with the catalytically active centers. Suitable passivating agents are, for example, silicon halides and silanes, e.g. silicon tetrachloride, chlorotrimethylsilane, dimethylaminotrichlorosilane or organometallic compounds of aluminum, boron and magnesium, for example trimethylaluminum, triethylaluminum, triisobutylaluminum, triethylborane, dibutylmagnesium. Chemical dehydration or passivation of the support material is carried out, for example, by reacting a suspension of the support material in a suitable solvent with the passivating reagent in pure form or as a solution in a suitable solvent with exclusion of air and moisture. Suitable solvents are, for example, aliphatic or aromatic hydrocarbons such as pentane, hexane, heptane, toluene and xylene. Passivation is carried out at from 25° C. to 120° C., preferably from 50° C. to 70° C. Higher and lower temperatures are possible. The reaction time is from 30 minutes to 20 hours, preferably from 1 to 5 hours. After the chemical dehydration is complete, the support material can be isolated by filtration under inert conditions, washed one or more times with suitable inert solvents as described above and subsequently dried in a stream of inert gas or under reduced pressure.

Organic support materials such as finely divided polyolefin powders (e.g. polyethylene, polypropylene or polystyrene) can also be used and should likewise be freed of adhering moisture, solvent residues or other impurities by appropriate purification and drying operations before use.

To apply the catalyst system of the present invention to a support, the catalyst mixture prepared as above is mixed with a dehydrated or passivated support material, the solvent is removed and the resulting supported metallocene catalyst system is dried to ensure that the solvent is completely or largely removed from the pores of the support material. The supported catalyst is obtained as a free-flowing powder.

The present invention also provides a process for preparing a polyolefin by polymerization of one or more olefins in the presence of the catalyst system of the present invention comprising at least one transition metal component of the formula (IV). For the purposes of the present invention, the term polymerization refers to both homopolymerization and copolymerization.

Preference is given to polymerizing olefins of the formula $R_m$—CH=CH—$R_n$, where $R_m$ and $R_n$ are identical or different and are each a hydrogen atom or a radical having from 1 to 20 carbon atoms, in particular from 1 to 10 carbon atoms, and $R_m$ and $R_n$ may, together with the atoms connecting them, form one or more rings.

Examples of such olefins are 1-olefins having 2–40 carbon atoms, preferably from 2 to 10 carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. In the process of the present invention, preference is given to homopolymerizing propene or ethene or copolymerizing propene with ethene and/or with one or more 1-olefins having from 4 to 20 carbon atoms, e.g. hexene, and/or one or more dienes having from 4 to 20 carbon atoms, e.g. 1,4-butadiene, norbornadiene, ethylidenenorbornene or ethylnorbornene. Examples of such copolymers are ethene-propene copolymers and ethene-propene-1,4-hexadiene terpolymers.

The polymerization is carried out at from −60° C. to 300° C., preferably from 50° C. to 200° C., very particularly preferably at 50° C.–80° C. The pressure is from 0.5 to 2000 bar, preferably from 5 to 64 bar.

The polymerization can be carried out in solution, in bulk, in suspension or in the gas phase, continuously or batchwise, in one or more stages.

The supported catalyst system can either be formed directly in the polymerization system or it can be resuspended as powder or while still moist with solvent and metered as a suspension in an inert suspension medium into the polymerization system.

A prepolymerization can be carried out using the catalyst system of the present invention. The prepolymerization is preferably carried out using the (or one of the) olefin(s) used in the polymerization.

To prepare olefin polymers having a broad molecular weight distribution, preference is given to using catalyst systems comprising two or more different transition metal compounds, e.g. metallocenes, and/or two or more different cocatalytically active organoelement compounds.

To remove catalyst poisons which may be present in the olefin, purification using an aluminum alkyl, for example trimethylaluminum, triethylaluminum or triisobutylaluminum, is advantageous. This purification can either be carried out in the polymerization system itself or the olefin is brought into contact with the Al compound and subsequently separated off again before introduction into the polymerization system.

As molar mass regulator and/or to increase the activity, hydrogen is added if necessary. The total pressure in the polymerization system is from 0.5 to 2500 bar, preferably from 2 to 1500 bar.

The catalyst system of the present invention is employed in a concentration, based on the transition metal, of preferably from $10^{-3}$ to $10^{-8}$ mol, preferably from $10^{-4}$ to $10^{-7}$ mol, of transition metal per $dm^3$ of solvent or per $dm^3$ of reactor volume.

Suitable solvents for preparing both the supported chemical compound of the present invention and the catalyst system of the present invention are aliphatic or aromatic solvents, for example hexane or toluene, ether solvents, for example tetrahydrofuran or diethyl ether, or halogenated hydrocarbons, for example methylene chloride, or halogenated aromatic hydrocarbons, for example o-dichlorobenzene.

Before addition of the catalyst system of the present invention or before activation of the catalyst system of the present invention in the polymerization system, it is additionally possible to introduce an alkylaluminum compound such as trimethylaluminum, triethylaluminum, triisobutylaluminum, trioctylaluminum or isoprenylaluminum into the reactor to make the polymerization system inert (for example to remove catalyst poisons present in the olefin). This is added to the polymerization system in a concentration of from 200 to 0.001 mmol of Al per kg of reactor contents. Preference is given to using triisobutylaluminum and triethylaluminum in a concentration of from 10 to 0.01 mmol of Al per kg of reactor contents, which makes it possible to choose a small Al/$M^1$ molar ratio in the synthesis of a supported catalyst system.

Furthermore, an additive such as an antistatic can be used in the process of the present invention, for example to improve the particle morphology of the olefin polymer. In general, all antistatics which are suitable for polymerization can be used. Examples of such antistatics are salt mixtures of calcium salts of Medialan acid and chromium salts of N-stearylanthranilic acid, which are described in DE-A-3, 543,360. Further suitable antistatics are, for example, isopropanol, $C_{12}$–$C_{22}$-fatty acid soaps of alkali metals or alkaline earth metals, salts of sulfonic esters, esters of polyethylene glycols with fatty acids, polyoxyethylene alkyl ethers, etc. An overview of antistatics is given in EP-A-0, 107,127.

A mixture of a metal salt of Medialan acid, a metal salt of anthranilic acid and a polyamine can also be used as antistatic, as described in EP-A-0,636,636. Commercially available products such as Stadis® 450 from DuPont, namely a mixture of toluene, isopropanol, dodecylbenzenesulfonic acid, a polyamine, a copolymer of 1-decene and $SO_2$ and also 1-decene or ASA®-3 from Shell and Atmer 163 from ICI can likewise be used.

The antistatic is preferably used as a solution; in the preferred case of isopropanol, Stadis® 450 and Atmer 163, preference is given to using from 1 to 50% by weight of this solution, preferably from 5 to 25% by weight, based on the mass of the supported catalyst used (support together with covalently bound compound capable of forming metallocenium ions and one or more metallocene compounds, e.g. of the formula X). However, the amounts of antistatic required may vary within a wide range depending on the type of antistatic used.

The actual polymerization is preferably carried out in liquid monomers (bulk) or in the gas phase.

The antistatic can be metered into the polymerization at any desired point in time. For example, a preferred procedure is to resuspend the supported catalyst system in an organic solvent, preferably an alkane such as heptane or isododecane. It is subsequently introduced while stirring into the polymerization autoclave. The antistatic is then metered in. The polymerization is carried out at from 0 to 100° C. A further preferred procedure is to meter the antistatic into the polymerization autoclave before addition of the supported catalyst system. The resuspended supported catalyst system is subsequently metered in while stirring at from 0 to 100° C. The polymerization time can be in the range from 0.1 to 24 hours. Preference is given to a polymerization time in the range from 0.1 to 5 hours.

In the above-described process, no deposits on the reactor are formed, no agglomerates are formed and the productivity of the catalyst system used is high. The polymers prepared using the process of the present invention have a narrow molecular weight distribution and a good particle morphology.

The polymers prepared using the catalyst system of the present invention have a uniform particle morphology and contain no fines. In the polymerization using the catalyst system of the present invention, no deposits or cake material occur.

The catalyst system of the present invention gives polymers, e.g. polypropylene, having extraordinarily high stereospecificity and regiospecificity.

The isotactic polypropylene which has been prepared using the catalyst system of the present invention has a proportion of 2-1-inserted propene units RI of <0.5% at a triad tacticity TT of >98.0% and a melting point of >156° C. The $M_w/M_n$ of the polypropylene prepared according to the present invention is from 2.5 to 3.5.

The novel compounds of the formulae (I) and (II) and also the catalyst systems derived therefrom are notable for the fact that the starting materials are not carcinogenic, teratogenic or extremely toxic. In addition, the good solubility of the ammonium tetraphenylborates described leads to virtually completely reacted catalyst systems. This criterion leads to considerable cost savings and thus to good commercial utilization.

The polymers prepared by the process of the present invention are, in particular, suitable for producing strong, hard and rigid shaped bodies such as fibers, filaments, injection-molded parts, films, plates or large hollow bodies (e.g. pipes).

The preparation of a possible catalyst system which has been described above in general terms can specifically be carried out according to the following sequence:

In a first Step A, an inorganic support material as described under C is reacted with a metal compound of the formula (IV). The metal compound of the formula (IV) is preferably added as a solution to a suspension of the support. Solvents or suspension media used are those described under B. The amount of metal compounds of the formula (IV) can vary within wide limits; the minimum amount depends on the number of hydroxyl groups on the support. The temperature, reaction times and pressures are not critical per se; preference is given to the temperatures and reaction times described under B. It has been found to be useful to remove the excess metal compound of the formula (IV) after the pretreatment of the support by washing, for example using hydrocarbons such as pentane, hexane, ethylbenzene or heptane, and to dry the support.

This material is then reacted in a further Step B with a metal complex of the formula (III) and a compound capable of forming metallocenium ions. It is also possible to use mixtures of various metallocene complexes.

As suitable compounds capable of forming metallocenium ions, use is made of the novel compounds of the formula (I) or (II). The conditions for the reaction of the metallocene complex with the compound of the formula (I) capable of forming metallocenium ions are not critical per se; preference is given to carrying out the reaction in solution, where suitable solvents are, in particular, hydrocarbons, preferably aromatic hydrocarbons such as toluene.

The material prepared as described in A is then added thereto. An amount of from 0.1 to 10% by weight of metallocene complexes, based on the inorganic support material, is particularly useful. The conditions for this reaction are likewise not critical; a temperature in the range from 20 to 80° C. and reaction times in the range from 0.1 to 20 hours have-been- found to-be-particularly useful.

In a further step C), namely the activation step, the material obtained as described in B) is reacted with a metal compound of the formula X. This activation can be carried out at any desired point in time, i.e. before, during or after the material obtained as described in B) is metered into the reactor. The activation is preferably carried out after the material obtained as described in B) has been metered into the reactor.

The activation compounds of the present invention have, in particular, a high activity, they can be stored for a long time, they are not pyrophoric and are readily soluble.

General procedures: preparation and handling of the compounds were carried out in the absence of air and moisture under argon (Schlenk technique). All solvents required were dried before use by boiling over suitable desiccants for a number of hours and subsequent distillation under argon. To characterize the compounds, samples were taken from the individual reaction mixtures and dried in an oil pump vacuum.

The following examples serve to illustrate the invention.

EXAMPLE 1

Synthesis of N,N-dimethylcyclohexylammonium hydrochloride 15.08 g of N,N-dimethylcyclohexylamine and 700 ml of heptane were placed under argon in a 500 ml three-necked flask fitted with internal thermometer and gas inlet stopcock. HCl gas from a gas generation apparatus was passed into this reaction mixture for 1 hour. The N,N-dimethylcyclohexylammonium hydrochloride formed was separated off via a G4 frit, washed with 100 ml of heptane and dried in an oil pump vacuum. 19.0 g (98%) of the desired product were isolated.

EXAMPLE 2

Synthesis of N,N-dimethylcyclohexylammonium tetrakis(pentafluorophenyl)borate

In a 1000 ml four-necked flask fitted with internal thermometer, stirrer and metal condenser, a solution of 20.87 g of N,N-dimethylcyclohexylammonium hydrochloride dissolved in 300 ml of dichloromethane was added dropwise at room temperature under argon to 111.2 g of lithium tetrakispentafluorophenylborate etherate. The reaction mixture was subsequently stirred for 4 hours. The insoluble lithium chloride was separated off via a G4 frit and washed twice with a total of 100 ml of dichloromethane. 200 ml of heptane were added to the dichloromethane of the filtrate and the dichloromethane was carefully removed at 35° C. and 450 mbar on a rotary evaporator. The precipitate formed was isolated via a G3 frit and washed twice with a total of 50 ml of heptane. The brownish crystalline product was dried in an oil pump vacuum and 72.5 g (74%) of product were isolated (purity by MMR: about 90%).

$^{19}$F-NMR in $CDCl_3$: −133.2 ppm (m, 8F), −163.3 ppm (m, 4F), −167.3 ppm (m, 8F)

EXAMPLE 3

Synthesis of N,N-dimethylbenzylammmonium hydrochloride 12.12 g of N,N-dimethylbenzylamine and 400 ml of heptane were placed under argon in a 500 ml three-necked flask fitted with internal thermometer and gas inlet stopcock. HCl gas from a gas generation apparatus was passed into this reaction mixture for 1 hour. The N,N-dimethylbenzylammonium hydrochloride formed was separated off via a G4 frit, washed with 100 ml of heptane and dried in an oil pump vacuum. 13.14 g (85%) of the desired product were isolated.

EXAMPLE 4

Synthesis of N,N-dimethylbenzylammonium tetrakis-(pentafluorophenyl)borate

In a 1000 ml four-necked flask fitted with internal thermometer, stirrer and metal condenser, a solution of 7.75 g of N,N-dimethylbenzylammonium hydrochloride dissolved in 116 ml of dichloromethane was added dropwise at room temperature under argon to 39.4 g of lithium tetrakispentafluorophenylborate etherate. The reaction mixture was subsequently stirred for 4 hours. The insoluble lithium chloride was separated off via a G4 frit and washed twice with a total of 100 ml [lacuna]. 200 ml of heptane were added to the dichloromethane of the filtrate and the dichloromethane was carefully removed at 35° C. and 450 mbar on a rotary evaporator. The precipitate formed was isolated via a G3 frit and washed twice with a total of 25 ml of heptane. The brownish crystalline product was dried in an oil pump vacuum and 34.51 g (93%) of product were isolated (purity by NMR: about 90%).

$^{19}$F-NMR in $CDCl_3$: −133.1 ppm (m, 8F), −163.3 ppm (m, 4F), −167.4 ppm (m, 8F)

EXAMPLE 5

Synthesis of N,N-dimethylisopropylammmonium hydrochloride 6 g of N,N-dimethylisopropylamine and 300 ml of heptane were placed under argon in a 500 ml three-necked flask fitted with internal thermometer and gas inlet stopcock. HCl gas from a gas generation apparatus was passed into this reaction mixture for 1 hour. The N,N-dimethylbenzylammonium hydrochloride formed was separated off via a G4 frit, washed with 100 ml of heptane and dried in an oil pump vacuum. 7.4 g (87%) of the desired product were isolated.

EXAMPLE 6

Synthesis of N,N-diisopropylbenzylammonium tetrakis(pentafluorophenyl)borate

In a 500 ml four-necked flask fitted with internal thermometer, stirrer and metal condenser, a solution of 7.4 g of N,N-dibenzylammonium hydrochloride dissolved in 116 ml of dichloromethane was added dropwise at room temperature under argon to 52.1 g of lithium tetrakispentafluorophenylborate etherate. The reaction mixture was subsequently stirred for 4 hours. The insoluble lithium chloride was separated off via a G4 frit and washed twice with a total of 100 ml of dichloromethane. 200 ml of heptane were added to the dichloromethane of the filtrate and the dichloromethane was carefully removed at 35° C. and 450 mbar on a rotary evaporator. The precipitate formed was isolated via a G3 frit and washed twice with a total of 25 ml of heptane. The brownish crystalline product was dried in an oil pump vacuum and 44.9 g (93%) of product were isolated (purity by NMR: about 90%).

$^{19}$F-NMR in $CDCl_3$: −133.1 ppm (m, 8F), −163.3 ppm (m, 4F), −167.4 ppm (m, 8F)

EXAMPLE 7

Preparation of a Catalyst a) Preparation of the Support Material 500 g of silica gel (type MS 948, from W. R. Grace, pore volume=1.6 ml/g, baked at 180° C. and about 2 mbar for 8 hours) were suspended in 4 l of dry heptane under an $N_2$ atmosphere. 2 l of triisobutylaluminum (2 molar in heptane, from Witco) were added at room temperature at such a rate that the temperature of the suspension did not exceed 30° C. The mixture was subsequently stirred for another 2 hours at room temperature, filtered and the filter cake was washed with 3 l of heptane. The solid was subsequently dried under reduced pressure.

b) Loading with Metallocene Complex 7.9 g of the deactivated silica gel prepared as described under a) were placed in a vessel which had previously been made inert and suspended in 40 ml of dry toluene. While stirring, 258 mg of dimethylcyclohexylammonium tetrakispentafluorophenylborate and 201 mg of rac-dimethylsilanediylbis(2-methyl-4-phenylindenyl)-zirconium dichloride were added to this suspension and the mixture was heated to 80° C. After a reaction time of 1.5 hours, the solvent was distilled off under reduced pressure. This gave a deep violet, free-flowing catalyst powder.

EXAMPLE 8

The procedure of Example 7 was repeated using 235 mg of dimethylsilanediylbis(2-methyl-4-(4'-tert-butylphenyl)indenyl)-zirconium dichloride.

EXAMPLE 9

The procedure of Example 7 was repeated using 237 mg of dimethylsilanediylbis(2-ethyl-4-(4'-tert-butylphenyl)indenyl)-zirconium dichloride.

EXAMPLE 10

The procedure of Example 7 was repeated using 238 mg of dimethylsilanediylbis(2-n-propyl-4-(4'-tert-butylphenyl)indenyl)-zirconium dichloride.

EXAMPLE 11

The procedure of Example 7 was repeated using 236 mg of dimethylsilanediylbis(2-methyl-4-naphthylindenyl)zirconium dichloride.

EXAMPLE 12

The procedure of Example 7 was repeated using 236 mg of dimethylsilanediyl(2-methyl-4-(4'-tert-butylphenyl)indenyl)-(2-isopropyl-4-(4'-tert-butylphenyl)indenyl)zirconium dichloride.

EXAMPLE 13

Propylene Polymerization 0.6 l of liquid propylene were in each case placed at room temperature in a 1 l steel autoclave which had been flushed with nitrogen. 4 mmol of triisobutylaluminum (2 molar solution in heptane) were added via a lock. After stirring for 5 minutes, 50 mg of the supported catalyst were likewise added via the lock and the autoclave was heated to 60° C. The polymer was obtained in the form of a free-flowing powder.

The following results were achieved:

TABLE 1

| Catalyst | Productivity g of PP/g of catalyst | MW (g/mol) | $M_w/M_n$ | Tm* (° C.) |
|---|---|---|---|---|
| Example 7 | 4800 | 801000 | 2.7 | 156.1 |
| Example 8 | 3700 | 453000 | 3.7 | 158.2 |
| Example 9 | 3600 | 368000 | 2.2 | 160.5 |
| Example 10 | 700 | 390000 | 2.7 | 159.1 |
| Example 11 | 1800 | 868000 | 2.3 | 155.0 |
| Example 12 | 2500 | 164000 | 1.9 | 155.5 |

*The melting point $T_m$ was determined by DSC measurement in accordance with IS Standard 3146 with a first heating at a heating rate of 20° C. per minute to 200° C., a dynamic crystallization at a cooling rate of 20° C. per minute to 25° C. and a second heating at a heating rate of 20° C. per minute up to 200° C. once again. The melting point is then the temperature at which the enthalpy versus temperature curve measured in the second heating has its maximum.

What is claimed is:

1. A chemical compound of formula I,

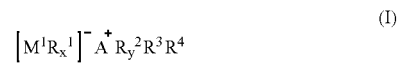

where
M$^1$ is boron,
x is 4,
y is 2,
A is nitrogen,
R$^1$ are identical or different and are each $C_6$–$C_{40}$-haloaryl, $C_6$–$C_{40}$-aryloxy, $C_7$–$C_{40}$-arylalkyl, $C_7$–$C_{40}$-haloarylalkyl, $C_7$–$C_{40}$-haloalkylaryl or $C_4$–$C_{40}$-cycloalkyl,
R$^2$ are identical or different and are each $C_1$–$C_6$-alkyl,
R$^3$ is $C_7$–$C_{20}$-arylalkyl, and
R$^4$ is a hydrogen atom.

2. A compound of formula I as claimed in claim 1, wherein R$^3$ is $C_7$-arylalkyl.

3. A compound of formula I as claimed in claim 1 which is
N,N-diethylbenzylammonium tetrakis(pentafluorophenyl)borate,
N,N-diisopropylbenzylammonium tetrakis(pentafluorophenyl)borate or
N,N-dimethylbenzylammonium tetrakis(pentafluorophenyl)borate.

4. A catalyst system comprising
A) at least one organometallic transition metal compound,
B) at least one compound of formula IV

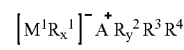

wherein R$^{20}$ are identical or different and are each halogen atoms, a hydrogen atom, $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl or $C_7$–$C_{40}$-haloalkylaryl,
C) at least one support component and
D) at least one compound of formula I

wherein
M$^1$ is boron,
x is 4,
y in 2,
A is nitrogen
R$^1$ are identical or different and are each $C_6$–$C_{40}$-haloaryl, $C_6$–$C_{40}$-aryloxy, $C_7$–$C_{40}$-arylalkyl, $C_7$–$C_{40}$-haloarylalkyl, $C_7$–$C_{40}$-haloalkylaryl or $C_4$–$C_{40}$-cycloalkyl,
R$^2$ are identical or different and are each $C_1$–$C_6$-alkyl,
R$^3$ is $C_7$–$C_{20}$-arylalkyl, or
R$^3$ is $C_3$–$C_9$-cycloalkyl which may be substituted by $C_1$–$C_{20}$-alkyl, $C_1C_{20}$haloalkyl, $C_1$–$C_{10}$-alkoxy, $C_6$–$C_{40}$-haloaryl, $C_7$–$C_{40}$-alkylaryl, $C_7$–$C_{40}$-arylalkyl, $C_7$–$C_{40}$-haloarylalkyl or $C_7$–$C_{40}$-haloalkylaryl, and $R^4$ is a hydrogen atom.

5. A catalyst system as claimed in claim 4, wherein at least one metallocene compound is used as the organometallic transition metal compound.

6. The catalyst system defined in claim 4, wherein $R^3$ is $C_3$–$C_9$-cycloalkyl or $C_7$-arylalkyl.

7. The catalyst system defined in claim 4, wherein $R^3$ is $C_7$–$C_{20}$-arylalkyl.

8. The catalyst system defined in claim 7, wherein $R^3$ is $C_7$-arylalkyl.

9. The catalyst system defined in claim 4, wherein at least one compound of formula I is selected from the group consisting of:

N,N-dimethylcyclohexylammonium tetrakis(pentafluorophenyl)borate,

N,N-diethylcyclohexylammonium tetrakis(pentafluorophenyl)borate,

N,N-diisopropylcyclohexylammonium tetrakis(pentafluorophenyl)borate,

N,N-diethylbenzylammonium tetrakis(pentafluorophenyl)borate,

N,N-diisopropylbenzylammonium tetrakis(pentafluorophenyl)borate, and

N,N-dimethylbenzylammonium tetrakis(pentafluorophenyl)borate.

10. The catalyst system defined in claim 4, wherein at least one compound of formula I is selected from the group consisting of:

N,N-diethylbenzylammonium tetrakis(pentafluorophenyl)borate,

N,N-diisopropylbenzylammonium tetrakis(pentafluorophenyl)borate and

N,N-dimethylbenzylammonium tetrakis(pentafluorophenyl)borate.

11. The catalyst system defined in claim 4, wherein $R^{20}$ of formula (IV) are identical or different and are each $C_1$–$C_6$-alkyl groups.

12. The catalyst system defined in claim 11, wherein $R^{20}$ of formula (IV) are identical or different and are each $C_1$–$C_4$-alkyl groups.

13. A process for preparing a polyolefin which comprises polymerizing of one or more olefins in the presence of a catalyst system as claimed in claim 4.

14. A process for preparing a polyolefin which comprises polymerizing one or more olefins in the presence of a catalyst system as claimed in claim 7.

* * * * *